US007371378B2

(12) United States Patent
Cohen et al.

(10) Patent No.: US 7,371,378 B2
(45) Date of Patent: May 13, 2008

(54) MODIFIED HUMAN IGF-IR ANTIBODIES

(75) Inventors: Bruce D. Cohen, East Lyme, CT (US); Vahe Bedian, East Lyme, CT (US)

(73) Assignee: Pfizer Inc., New York, NY (US)

( * ) Notice: Subject to any disclaimer, the term of this patent is extended or adjusted under 35 U.S.C. 154(b) by 186 days.

(21) Appl. No.: 10/917,073

(22) Filed: Aug. 12, 2004

(65) Prior Publication Data

US 2005/0069539 A1    Mar. 31, 2005

Related U.S. Application Data

(60) Provisional application No. 60/495,200, filed on Aug. 13, 2003.

(51) Int. Cl.
    *A61K 39/395*   (2006.01)
    *C07K 16/00*    (2006.01)
    *C07K 16/28*    (2006.01)
(52) U.S. Cl. .............................. 424/130.1; 424/141.1; 424/143.1; 530/387.1; 530/388.1; 530/388.22
(58) Field of Classification Search ............. 424/130.1, 424/141.1, 143.1; 530/387.1, 141.1, 143.1
See application file for complete search history.

(56) References Cited

U.S. PATENT DOCUMENTS

| 6,054,561 | A | 4/2000 | Kucherlapati et al. | |
|---|---|---|---|---|
| 6,146,629 | A | 11/2000 | Dagan ..................... | 424/149.1 |
| 6,657,103 | B1 | 12/2003 | Kucherlapati et al. | |
| 6,682,736 | B1* | 1/2004 | Hanson et al. ........... | 424/144.1 |
| 2003/0165502 | A1 | 9/2003 | Fujita-Yamaguchi | |
| 2003/0235582 | A1 | 12/2003 | Singh ..................... | 424/141.1 |
| 2004/0086503 | A1 | 5/2004 | Cohen et al. ............ | 424/143.1 |
| 2004/0202655 | A1 | 10/2004 | Morton et al. | |

FOREIGN PATENT DOCUMENTS

| WO | WO 9109967 | 7/1991 |
|---|---|---|
| WO | WO 9317105 | 9/1993 |
| WO | WO 96/33735 | * 10/1996 |
| WO | WO 9633735 | 10/1996 |
| WO | WO 99060023 | 11/1999 |
| WO | WO 0056772 | 9/2000 |
| WO | WO 02053596 | 7/2002 |
| WO | WO 03059951 | 7/2003 |
| WO | WO 03093317 | 11/2003 |
| WO | WO 03100008 | 12/2003 |
| WO | WO 03100059 | 12/2003 |
| WO | WO 03106621 | 12/2003 |
| WO | WO 04071529 | 8/2004 |
| WO | WO 04087756 | 12/2004 |

OTHER PUBLICATIONS

Kobrin et al, J Immunology 146: 2017-2020, 1991.*
Zhu et al, Investigational New Drugs 17: 195-212, 1999.*
Mitsiades, C., et al., The IGF/IGF-1R system is a major therapeutic target for multiple myeloma, other hematologic malignancies and solid tumors, Blood, vol. 100, No. 11, Nov. 16, 2004 p. 170A, XP002293672, abstract.
Mitsiades, C., et al., Gene expression and proteomic profiling of multiple myeloma (MM) cells co-cultured with bone marrow (BM) stromal cells or stimulated with BM-derived cytokines: Implications for therapeutic targeting of the BM milieu in MM, Blood, vol. 100, No. 11, Nov. 16, 2002, p. 811A, XP002293673, abstract.
Elagiab, K., et al., Immunoglobulin variable genes and epitope recognition of human monoclonal anti-Ro 52-kd in primary Sjogren's syndrome, Arthritis and Rheumatism, vol. 42, No. 11, Nov. 1999, pp. 2471-2481, XP002293674, abstract.
Aburatani, T., et al., Importance of CDR H3 basal residue in VH/VL interaction of human antibodies, Journal of Biochemistry, vol. 132, No. 5, Nov. 2002, pp. 775-782, XP002293675.
Li, S., et al., Single-chain antibodies against human insulin-like growth factor I receptor: expression, purification, and effect on tumor growth, Cancer Immunol Immunother, Jul. 2000, 49: pp. 243-252, XP001113064.
Hermanto, U., et al., Inhibition of mitogen-activated protein kinase selectively inhibits cell proliferation in human breast cancer cells displaying enhanced insulin-like growth factor I-mediated mitogen-activated protein kinase activation, Cell Growth & Differentiation: The Molecular Biology Journal of the American Association for Cancer Research, Dec. 2000, vol. 11, No. 12, pp. 655-664, XP002229921.
DiGiovanni, J., et al., Deregulated expression of insulin-like growth factor 1 in prostate epithelium leads to neoplasia in transgenic mice, Proc. Natl. Acad. Sci., 97: pp. 3455-3460.
Drexhage, H.A., & Wulffraat, N.M., Endocrine autoimmune disease, Netherlands Journal of Medicine, 45: pp. 285-293, (1994).
Kim, B., et al., Insulin receptor substrate 2 and shc play different roles in insulin-like growth factor I signaling, Journal of Biological Chemistry, 273 pp. 34543-34550 (1998).
Smith, L.E., et al., Regulation of vascular endothelial growth factor-dependent retinal neovascularization by insulin-like growth factor-1 receptor, Nature Medicine, 5: pp. 1390-1395 (1999).
Tappy, et al, Antibodies to insulin-like growth factor I receptors in diabetes and other disorders, Diabetes, 37: pp. 1708-1714 (1998).
Thompson, K., et al., Low prevalence of autoantibodies to the insulin-like growth factor I receptor in children with short stature, Pediatric Research, 32: pp. 455-459 (1992).
Weightman, D.R., et al., Autoantibodies to IGF-1 binding sites in thyroid associated opthalmopathy, Autoimmunity, 16: pp. 251-257 (1993).

(Continued)

*Primary Examiner*—Christina Chan
*Assistant Examiner*—Phuong Huynh
(74) *Attorney, Agent, or Firm*—Austin W. Zhang; Pamela G. Salkeld; Bryan C. Zielinski

(57) ABSTRACT

The present invention relates to antibodies, which are directed to the human IGF-1 receptor (IGF-1R) and are to be administered for the treatment of cancer. The antibodies of the present invention have been altered to comprise antibodies with one or more selected germlne framework amino acid residues which replace one or more corresponding somatically mutated residues in the variable region of the unaltered antibody. The modification results in the framework region mutations converted to germline. The modification results in a reduced propensity for the antibody to elicit an immune response (reduced immunogenicity) following administration to a human subject.

5 Claims, 13 Drawing Sheets

OTHER PUBLICATIONS

Wraight, C., et al., Reversal of epidermal hyperproliferation in psoriasis by insulin-like growth factor I receptor antisense oligonucleotides, Nature Biotechnology, 18: pp. 521-526 (2000).

Paul, W. E., Fundamental Immunology 242 (ed., 3d ed. 1993).

Rudikoff, S., et al., Single amino acid substitution altering antigen-binding specificity, Proc Natl Acad Sci USA, vol. 79, pp. 1978—1983 (1982).

Groves, D.J., et al., Production of an Ovine Monoclonal Antibody to Testoserone by an Interspecies Fusion, Hybridoma, vol. 6, pp. 71-76 (1987).

Rubini, M, et al., Characterization of an Antibody that can Detect and Activated IGF-I Receptor in Human Cancers, Experimental Cell Research 251, pp. 22-32 (1999).

Colman, P.M., Effect of amino acid sequence changes on antibody-antigen interactions, Research in Immunology, vol. 145, pp. 33-36 (1994).

* cited by examiner

FIG. 1

```
ATGGAGTTTG GGCTGAGCTG GGTTTTCCTT GTTGCTATTA TAAAAGGTGT    50
CCAGTGTCAG GTGCAGCTGG TGGAGTCCGG GGGAGGCTTG GTCAAGCCTG   100
GAGGGTCCCT GAGACTCTCC TGTGCAGCCT CTGGATTCAC TTTCAGTGAC   150
TACTATATGA GCTGGATCCG CCAGGCTCCA GGGAAGGGGC TGGAATGGGT   200
TTCATACATT AGTAGTAGTG GTAGTACCAG AGACTACGCA GACTCTGTGA   250
AGGGCCGATT CACCATCTCC AGGGACAACG CCAAGAACTC ACTGTATCTG   300
CAAATGAACA GCCTGAGAGC CGAGGACACG GCCGTGTATT ACTGTGTGAG   350
AGATGGAGTG GAAACTACTT TTTACTACTA CTACTACGGT ATGGACGTCT   400
GGGGCCAAGG GACCACGGTC ACCGTCTCCT CAGCCTCCAC CAAGGGCCCA   450
TCGGTCTTCC CCCTGGCGCC CTGCTCCAGG AGCACCTCCG AGAGCACAGC   500
GGCCCTGGGC TGCCTGGTCA AGGACTACTT CCCCGAACCG GTGACGGTGT   550
CGTGGAACTC AGGCGCTCTG ACCAGCGGCG TGCACACCTT CCCAGCTGTC   600
CTACAGTCCT CAGGACTCTA CTCCCTCAGC AGCGTGGTGA CCGTGCCCTC   650
CAGCAACTTC GGCACCCAGA CCTACACCTG CAACGTAGAT CACAAGCCCA   700
GCAACACCAA GGTGGACAAG ACAGTTGAGC GCAAATGTTG TGTCGAGTGC   750
CCACCGTGCC CAGCACCACC TGTGGCAGGA CCGTCAGTCT TCCTCTTCCC   800
CCCAAAACCC AAGGACACCC TCATGATCTC CCGGACCCCT GAGGTCACGT   850
GCGTGGTGGT GGACGTGAGC CACGAAGACC CCGAGGTCCA GTTCAACTGG   900
TACGTGGACG GCGTGGAGGT GCATAATGCC AAGACAAAGC CACGGGAGGA   950
GCAGTTCAAC AGCACGTTCC GTGTGGTCAG CGTCCTCACC GTTGTGCACC  1000
AGGACTGGCT GAACGGCAAG GAGTACAAGT GCAAGGTCTC CAACAAAGGC  1050
CTCCCAGCCC CCATCGAGAA AACCATCTCC AAAACCAAAG GGCAGCCCCG  1100
AGAACCACAG GTGTACACCC TGCCCCCATC CCGGGAGGAG ATGACCAAGA  1150
ACCAGGTCAG CCTGACCTGC CTGGTCAAAG GCTTCTACCC CAGCGACATC  1200
GCCGTGGAGT GGGAGAGCAA TGGGCAGCCG GAGAACAACT ACAAGACCAC  1250
ACCTCCCATG CTGGACTCCG ACGGCTCCTT CTTCCTCTAC AGCAAGCTCA  1300
CCGTGGACAA GAGCAGGTGG CAGCAGGGGA ACGTCTTCTC ATGCTCCGTG  1350
ATGCATGAGG CTCTGCACAA CCACTACACG CAGAAGAGCC TCTCCCTGTC  1400
TCCGGGTAAA TGA                                         1413
```

FIG. 2

```
ATGGACATGA GGGTCCCCGC TCAGCTCCTG GGCTCCTGC  TGCTCTGGTT   50
CCCAGGTGCC AGGTGTGACA TCCAGATGAC CCAGTCTCCA TCCTCCCTGT  100
CTGCATCTGT AGGAGACAGA GTCACCATCA CTTGCCGGGC AAGTCAGGAC  150
ATTAGACGTG ATTTAGGCTG GTATCAGCAG AAACCAGGGA AAGCTCCTAA  200
GCGCCTGATC TATGCTGCAT CCCGTTTACA AAGTGGGGTC CCATCAAGGT  250
TCAGCGGCAG TGGATCTGGG ACAGAATTCA CTCTCACAAT CAGCAGCCTG  300
CAGCCTGAAG ATTTTGCAAC TTATTACTGT CTACAGCATA ATAATTATCC  350
TCGGACGTTC GGCCAAGGGA CCAAGGTGGA AATCAAACGA ACTGTGGCTG  400
CACCATCTGT CTTCATCTTC CCGCCATCTG ATGAGCAGTT GAAATCTGGA  450
ACTGCCTCTG TTGTGTGCCT GCTGAATAAC TTCTATCCCA GAGAGGCCAA  500
AGTACAGTGG AAGGTGGATA ACGCCCTCCA ATCGGGTAAC TCCCAGGAGA  550
GTGTCACAGA GCAGGACAGC AAGGACAGCA CCTACAGCCT CAGCAGCACC  600
CTGACGCTGA GCAAAGCAGA CTACGAGAAA CACAAAGTCT ACGCCTGCGA  650
AGTCACCCAT CAGGGCCTGA GCTCGCCCGT CACAAAGAGC TTCAACAGGG  700
GAGAGTGTTA GTGACCCGGG AACGACCG                           728
```

FIG. 3

```
MEFGLSWVFL VAIIKGVQCQ AQLVESGGGL VKPGGSLRLS CAASGFTFSD YMSWIRQAP GKGLEWVSYI SSSGSTRDYA DSVKGRFTIS RDNAKNSLYL
MEFGLSWVFL VAIIKGVQCQ VQLVESGGGL VKPGGSLRLS CAASGFTFSD YMSWIRQAP GKGLEWVSYI SSSGSTIYYA DSVKGRFTIS RDNAKNSLYL

QMNSLRAEDT AVYYCVR--D GVETTF-YYY YYGMDVWGQG TTVTVSSAST KGPSVFPLAP CSRSTSESTA ALGCLVKDYF PEPVTVSWNS GALTSGVHTF
QMNSLRAEDT AVYYCARVLR FLEMLLYYYY YYGMDVWGQG TTVTVSSAST KGPSVFPLAP CSRSTSESTA ALGCLVKDYF PEPVTVSWNS GALTSGVHTF

PAVLQSSGLY SLSSVVTVPS SNFGTQTYTC NVDHKPSNTK VDKTVERKCC VECPPCPAPP VAGPSVFLFP PKPKDTLMIS RTPEVTCVVV DVSHEDPEVQ
PAVLQSSGLY SLSSVVTVPS SNFGTQTYTC NVDHKPSNTK VDKTVERKCC VECPPCPAPP VAGPSVFLFP PKPKDTLMIS RTPEVTCVVV DVSHEDPEVQ

FNWYVDGVEV HNAKTKPREE QFNSTFRVVS VLTVVHQDWL NGKEYKCKVS NKGLPAPIEK TISKTKGQPRE PQVYTLPPS REEMTKNQVS LTCLVKGFYP
FNWYVDGVEV HNAKTKPREE QFNSTFRVVS VLTVVHQDWL NGKEYKCKVS NKGLPAPIEK TISKTKGQPRE PQVYTLPPS REEMTKNQVS LTCLVKGFYP

SDIAVEWESN GQPENNYKTT PPMLDSDGSF FLYSKLTVDK SRWQQGNVFS CSVMHEALHN HYTQKSLSLSP GK
SDIAVEWESN GQPENNYKTT PPMLDSDGSF FLYSKLTVDK SRWQQGNVFS CSVMHEALHN HYTQKSLSLSP GK
```

FIG. 4

```
MDMRVPAQLL GLLLLWFPGA RCDIQMTQSP SSLSASVGDR VTFTCRASQD IRRDLGWYQQ KPGKAPKRLI YAASRLQSGV PSRFSGSGSG TEFTLTISSL
MDMRVPAQLL GLLLLWFPGA RCDIQMTQSP SSLSASVGDR VTITCRASQG IRNDLGWYQQ KPGKAPKRLI YAASSLQSGV PSRFSGSGSG TEFTLTISSL

QPEDFATYYC LQHNNYPRTF GQGTEVEIIR TVAAPSVFIF PPSDEQLKSG TASVVCLLNN FYPREAKVQW KVDNALQSGN SQESVTEQDS KDSTYSLSST
QPEDFATYYC LQHNSYPWTF GQGTKVEIKR TVAAPSVFIP PPSDEQLKSG TASVVCLLNN FYPREAKVQW KVDNALQSGN SQESVTEQDS KDSTYSLSST

LTLSKADYEK HKVYACEVTH QGLSSPVTKS FNRGRC
LTLSKADYEK HKVYACEVTH QGLSSPVTKS FNRGEC
```

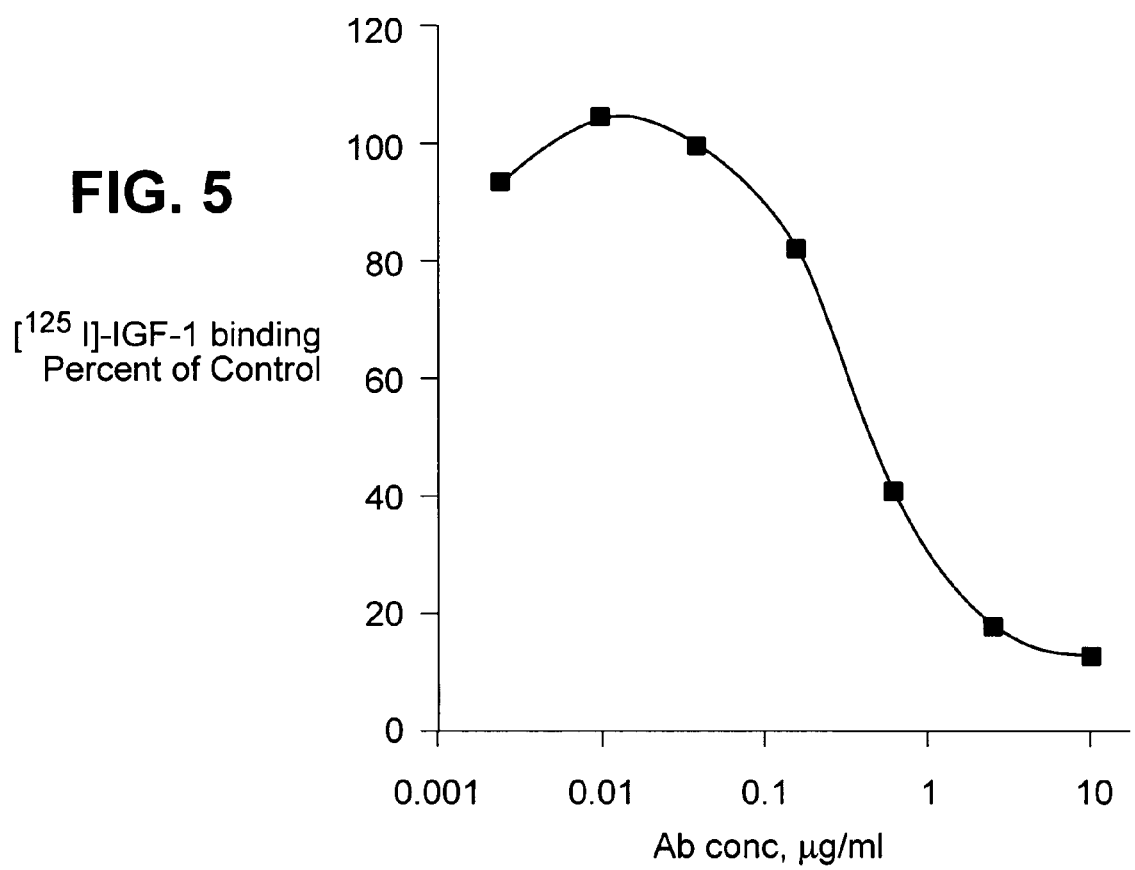

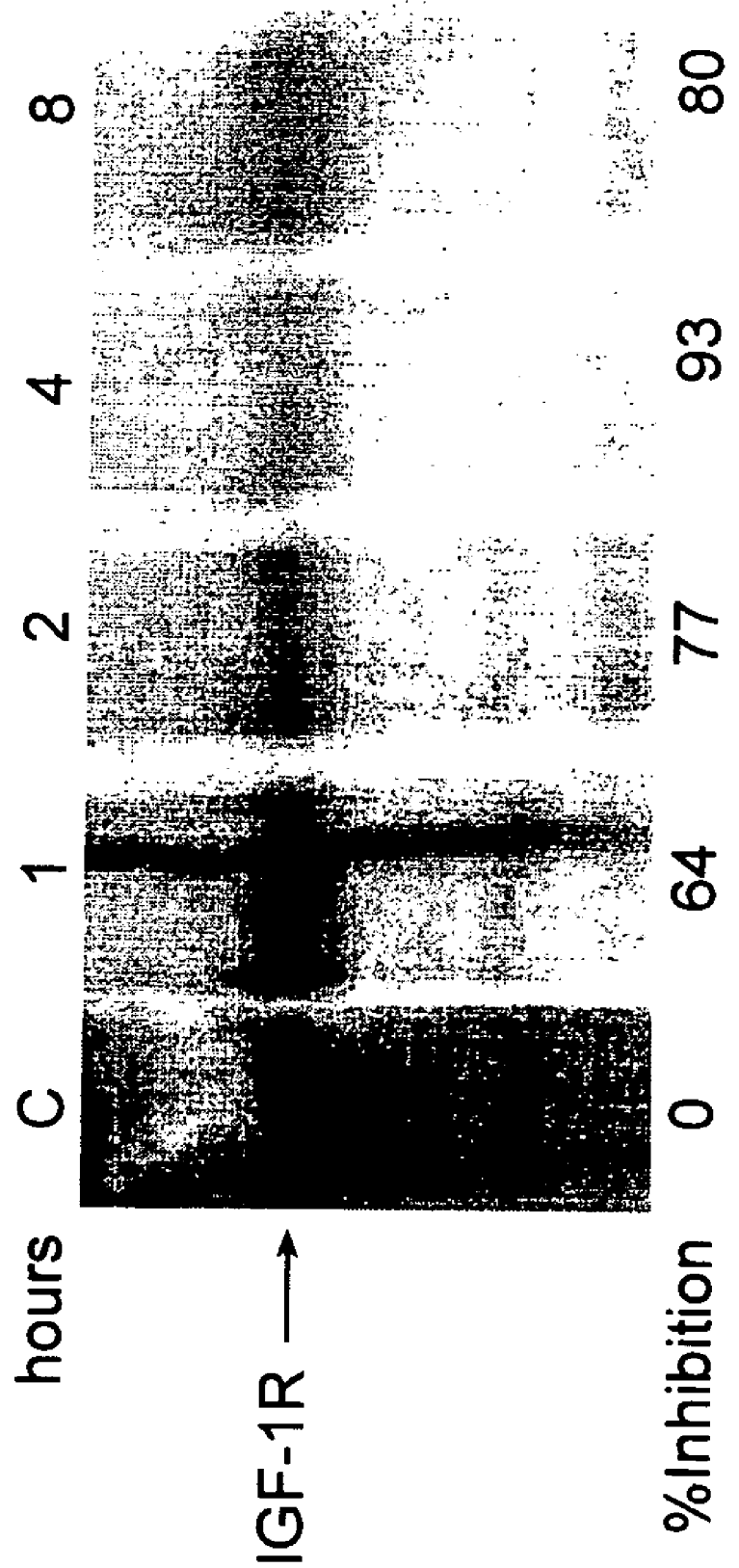

FIG. 8B

Tumor volume, mm³ vs Time, days

Legend:
- Control
- 31 μg Ab + Adria
- 62 μg Ab + Adria
- 125 μg Ab + Adria
- 250 μg Ab + Adria
- 7.5 mg/kg Adria

SEQUENCE LISTING

<160> NUMBER OF SEQ ID NOS: 6

<210> SEQ ID NO 1
<211> LENGTH: 1413
<212> TYPE: DNA
<213> ORGANISM: Homo sapiens

<400> SEQUENCE: 1

```
atggagtttg ggctgagctg ggttttcctt gttgctatta taaaaggtgt ccagtgtcag      60
gtgcagctgg tggagtccgg gggaggcttg gtcaagcctg gagggtccct gagactctcc     120
tgtgcagcct ctggattcac tttcagtgac tactatatga gctggatccg ccaggctcca     180
gggaaggggc tggaatgggt tcatacatt agtagtagtg gtagtaccag agactacgca     240
gactctgtga agggccgatt caccatctcc agggacaacg ccaagaactc actgtatctg     300
caaatgaaca gcctgagagc cgaggacacg gccgtgtatt actgtgtgag agatggagtg     360
gaaactactt tttactacta ctactacggt atggacgtct ggggccaagg gaccacggtc     420
accgtctcct cagcctccac caagggccca tcggtcttcc cctggcgcc ctgctccagg     480 agcacctccg agagcacagc ggccctgggc tgcctggtca aggactactt ccccgaaccg     540
gtgacggtgt cgtggaactc aggcgctctg accagcggcg tgcacacctt cccagctgtc     600
ctacagtcct caggactcta ctccctcagc agcgtggtga ccgtgccctc agcaacttc     660 ggcacccaga cctacacctg caacgtagat cacaagccca gcaacaccaa ggtggacaag     720
acagttgagc gcaaatgttg tgtcgagtgc ccaccgtgcc cagcaccacc tgtggcagga     780
ccgtcagtct tcctcttccc cccaaaaccc aaggacaccc tcatgatctc ccggacccct     840
gaggtcacgt gcgtggtggt ggacgtgagc cacgaagacc ccgaggtcca gttcaactgg     900
tacgtggacg gcgtggaggt gcataatgcc aagacaaagc cacgggagga gcagttcaac     960
agcacgttcc gtgtggtcag cgtcctcacc gttgtgcacc aggactggct gaacggcaag    1020
gagtacaagt gcaaggtctc caacaaaggc ctcccagccc ccatcgagaa aaccatctcc    1080
aaaaccaaag gcagccccg agaaccacag gtgtacaccc tgcccccatc ccgggaggag    1140
atgaccaaga accaggtcag cctgacctgc ctggtcaaag gcttctaccc cagcgacatc    1200
gccgtggagt gggagagcaa tgggcagccg gagaacaact acaagaccac acctcccatg    1260
ctggactccg acggctcctt cttcctctac agcaagctca ccgtggacaa gagcaggtgg    1320
cagcagggga acgtcttctc atgctccgtg atgcatgagg ctctgcacaa ccactacacg    1380
cagaagagcc tctccctgtc tccgggtaaa tga                                1413
```

<210> SEQ ID NO 2
<211> LENGTH: 728
<212> TYPE: DNA

<213> ORGANISM: Homo sapiens

<400> SEQUENCE: 2

```
atggacatga gggtccccgc tcagctcctg gggctcctgc tgctctggtt cccaggtgcc    60
aggtgtgaca tccagatgac ccagtctcca tcctccctgt ctgcatctgt aggagacaga   120
gtcaccatca cttgccgggc aagtcaggac attagacgtg atttaggctg gtatcagcag   180
aaaccaggga agctcctaa gcgcctgatc tatgctgcat cccgtttaca agtgggggtc    240
ccatcaaggt tcagcggcag tggatctggg acagaattca ctctcacaat cagcagcctg   300
cagcctgaag attttgcaac ttattactgt ctacagcata taattatcc tcggacgttc    360
ggccaaggga ccaaggtgga aatcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta gtgacccggg   720
aacgaccg                                                            728
```

<210> SEQ ID NO 3
<211> LENGTH: 470
<212> TYPE: PRT
<213> ORGANISM: Homo sapiens

<400> SEQUENCE: 3

```
Met Glu Phe Gly Leu Ser Trp Val Phe Leu Val Ala Ile Ile Lys Gly
  1               5                  10                  15

Val Gln Cys Gln Val Gln Leu Val Glu Ser Gly Gly Gly Leu Val Lys
             20                  25                  30

Pro Gly Gly Ser Leu Arg Leu Ser Cys Ala Ala Ser Gly Phe Thr Phe
         35                  40                  45

Ser Asp Tyr Tyr Met Ser Trp Ile Arg Gln Ala Pro Gly Lys Gly Leu
     50                  55                  60

Glu Trp Val Ser Tyr Ile Ser Ser Ser Gly Ser Thr Arg Asp Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr Tyr Cys Ala Arg Asp Gly Val Glu Thr Thr Phe Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220
```

```
Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Gln Phe Asn Trp Tyr Val Asp Gly
290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
                340                 345                 350

Ala Pro Ile Glu Lys Thr Ile Ser Lys Thr Lys Gly Gln Pro Arg Glu
            355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 4
<211> LENGTH: 473
<212> TYPE: PRT
<213> ORGANISM: Homo sapiens

<400> SEQUENCE: 4

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Val Leu Arg Phe Leu Glu Trp Leu Leu Tyr Tyr
```

-continued

```
            115                 120                 125
Tyr Tyr Tyr Tyr Gly Met Asp Val Trp Gly Gln Gly Thr Thr Val Thr
        130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
    210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Asn Ser Thr Phe Arg Val Val Ser Val Leu Thr Val Val His
                325                 330                 335

Gln Asp Trp Leu Asn Gly Lys Glu Tyr Lys Cys Lys Val Ser Asn Lys
            340                 345                 350

Gly Leu Pro Ala Pro Ile Glu Lys Thr Ile Ser Lys Thr Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Met Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 5
<211> LENGTH: 236
<212> TYPE: PRT
<213> ORGANISM: Homo sapiens

<400> SEQUENCE: 5

Met Asp Met Arg Val Pro Ala Gln Leu Leu Gly Leu Leu Leu Leu Trp
1               5                   10                  15
```

```
Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Arg Arg Asp Leu Gly Trp Tyr Gln Gln Lys Pro Gly Lys
50                  55                  60

Ala Pro Lys Arg Leu Ile Tyr Ala Ala Ser Arg Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
                100                 105                 110

His Asn Asn Tyr Pro Arg Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 6
<211> LENGTH: 236
<212> TYPE: PRT
<213> ORGANISM: Homo sapiens

<400> SEQUENCE: 6

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
                100                 105                 110

His Asn Ser Tyr Pro Trp Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160
```

-continued

```
Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235
```

MODIFIED HUMAN IGF-IR ANTIBODIES

BACKGROUND OF THE INVENTION

This application claims the benefit of U.S. Provisional Application 60/495,200, filed Aug. 13, 2003, which application is hereby incorporated by reference.

Insulin-like growth factor (IGF-I) is a 7.5-kDa polypeptide that circulates in plasma in high concentrations and is detectable in most tissues. IGF-I stimulates cell differentiation and cell proliferation, and is required by most mammalian cell types for sustained proliferation. These cell types include, among others, human diploid fibroblasts, epithelial cells, smooth muscle cells, T lymphocytes, neural cells, myeloid cells, chondrocytes, osteoblasts and bone marrow stem cells.

The first step in the transduction pathway leading to IGF-I-stimulated cellular proliferation or differentiation is binding of IGF-I or IGF-II (or insulin at supraphysiological concentrations) to the IGF-I receptor. The IGF-I receptor is composed of two types of subunits: an alpha subunit (a 130-135 kDa protein that is entirely extracellular and functions in ligand binding) and a beta subunit (a 95-kDa transmembrane protein, with transmembrane and cytoplasmic domains). The IGF-IR belongs to the family of tyrosine kinase growth factor receptors (Ullrich et al., Cell 61: 203-212, 1990), and is structurally similar to the insulin receptor (Ullrich et al., EMBO J. 5: 2503-2512, 1986). The IGF-IR is initially synthesized as a single chain proreceptor polypeptide, which is processed by glycosylation, proteolytic cleavage, and covalent bonding to assemble into a mature 460-kDa heterotetramer comprising two alpha-subunits and two beta-subunits. The beta subunit(s) possesses ligand-activated tyrosine kinase activity. This activity is implicated in the signaling pathways mediating ligand action which involve autophosphorylation of the beta-subunit and phosphorylation of IGF-IR substrates.

There is considerable evidence for a role for IGF-I and/or IGF-IR in the maintenance of tumor cells in vitro and in vivo. IGF-IR levels are elevated in tumors of lung (Kaiser et al., J. Cancer Res. Clin Oncol. 119: 665-668, 1993; Moody et al., Life Sciences 52: 1161-1173, 1993; Macauley et al., Cancer Res., 50: 2511-2517, 1990), breast (Pollak et al., Cancer Lett. 38: 223-230, 1987; Foekens et al., Cancer Res. 49: 7002-7009, 1989; Cullen et al., Cancer Res. 49: 7002-7009, 1990; Arteaga et al., J. Clin. Invest. 84: 1418-1423, 1989), prostate and colon (Remaole-Bennet et al., J. Clin. Endocrinol. Metab. 75: 609-616, 1992; Guo et al., Gastroenterol. 102: 1101-1108, 1992). Deregulated expression of IGF-I in prostate epithelium leads to neoplasia in transgenic mice (DiGiovanni et al., Proc. Natl. Acad. Sci. USA 97: 3455-60, 2000). In addition, IGF-I appears to be an autocrine stimulator of human gliomas (Sandberg-Nordqvist et al., Cancer Res. 53: 2475-2478, 1993), while IGF-I stimulated the growth of fibrosarcomas that overexpressed IGF-IR (Butler et al., Cancer Res. 58: 3021-27, 1998). Further, individuals with "high normal" levels of IGF-I have an increased risk of common cancers compared to individuals with IGF-I levels in the "low normal" range (Rosen et al., Trends Endocrinol. Metab. 10: 136-41, 1999). For a review of the role IGF-I/IGF-I receptor interaction plays in the growth of a variety of human tumors, see Macaulay, Br. J. Cancer, 65: 311-320, 1992.

Caloric restriction is the most effective and reproducible intervention for increasing the life span in a variety of animal species, including mammals. It is also the most potent, broadly acting cancer-prevention regimen in experimental carcinogenesis models. A key biological mechanism underlying many of its beneficial effects is the insulin-like growth factor-1 pathway (Hursting et al., Annu. Rev. Med. 54:131-52, 2003).

EP0629240B1 refers to the conversion of an antibody sequence by recombinant DNA technology to the germlne sequence to attempt to decrease immunogenicity when administered to a patient. WO02/066058A1 refers to antibodies directed to the EGF receptor (HER1) that are otherwise modified to reduce their propensity to elicit an immune response.

In view of the roles that IGF-I and IGF-IR have in such disorders as cancer and other proliferative disorders when IGF-I and/or IGF-IR are overexpressed, and the roles that too little IGF-I and IGF-IR have in disorders when either IGF-I and/or IGF-IR are underexpressed, it is desirable to generate antibodies to IGF-IR that could be used to either inhibit or stimulate IGF-IR. Such antibodies are described, for example, in WO 02/05359, published Jul. 11, 2002. The text of this publication, including all sequences described, is hereby incorporated by reference.

SUMMARY OF THE INVENTION

The present invention provides a modified human monoclonal antibody or antigen-binding portion thereof in which at least one somatically mutated amino acid sequence is converted to germline amino acid sequence. Preferably the replaced residue is contained in a variable region of the antibody and more preferably the replaced residue is contained in a framework region of the variable region.

Preferably the human antibody or antigen-binding portion of the present invention specifically binds to human insulin-like growth factor I receptor (IGF-IR).

In one embodiment the sequence of the variable region of the light chain of the antibody comprises three framework mutations reverted back to an amino acid sequence encoded by a germ line A30 gene. In a preferred embodiment, the variable region of the light chain comprises amino acid numbers 23 to 130 of amino acid sequence of SEQ ID NO: 5. In an even more preferred embodiment, the light chain of the human antibody comprises amino acid numbers 23 to 236 of SEQ ID NO: 5.

In another embodiment of the invention the sequence of the variable region of a heavy chain of the antibody comprises two framework mutations reverted back to amino acid sequence encoded by a germ line DP-35 gene. In a preferred embodiment, the variable region of the heavy chain comprises amino acid numbers 20 to 144 of SEQ ID NO: 3. In an even more preferred embodiment, the heavy chain of the human antibody comprises amino acid numbers 20 to 470 of SEQ ID NO: 3 and the light chain comprises amino acid numbers 23 to 236 of SEQ ID NO: 5.

In another embodiment, the heavy chain of the antibody of the invention lacks a terminal lysine.

The invention also relates to a pharmaceutical composition for the treatment of cancer where the pharmaceutical composition comprises the modified human antibody of the invention in combination with an antineoplastic, chemotherapeutic or anti-tumor agent and a pharmaceutically acceptable carrier.

The invention also relates to a method of treating cancer in a human with the human antibody comprising the step of administering to a human an amount of the antibody that is effective to treat said cancer. In one embodiment, the invention relates to a treatment comprising the step of administering an anti-neoplastic, anti-tumor, anti-angiogenic or chemotherapeutic agent in conjunction with the antibody of the present invention.

The invention also relates to a method of treating a patient in need thereof with the antibody by administering to the patient an effective amount of the antibody. In one embodiment, the invention relates to a treatment comprising the step of administering an anti-neoplastic, anti-tumor, anti-angiogenic or chemotherapeutic agent in conjunction with the antibody of the present invention.

The invention also relates to an isolated polynucleotide that comprises a nucleic acid sequence that encodes a heavy chain or antigen-binding portion thereof or a light chain or antigen-binding portion thereof of the antibody of the present invention. In one embodiment of the invention, the invention also provides a method for treating a subject in need thereof with an effective amount of a nucleic acid molecule encoding the heavy and/or light chain or antigen-binding portions thereof of an anti-IGF-IR antibody.

The invention provides a vector comprising the isolated nucleic acid molecule and a host cell comprising the vector. The invention further comprises a host cell that produces an antibody that has the same amino acid sequences as the mature heavy and light chains of 2.12.1fx.

The invention also provides a method of recombinantly producing and culturing the antibody encoded by the nucleic acid molecule.

The invention also relates to diagnostic methods for diagnosing the presence or location of an IGF-IR-expressing tissue using an anti-IGF-IR antibody.

BRIEF DESCRIPTION OF THE DRAWINGS

FIG. 1 shows the DNA sequence encoding the heavy chain of antibody 2.12.1fx, including the sequence encoding the signal sequence used to express the mature antibody (SEQ ID NO: 1).

FIG. 2 shows the DNA sequence encoding the light chain of antibody 2.12.1fx, including the sequence encoding the signal sequence used to express the mature antibody (SEQ ID NO: 2).

FIG. 3 shows an alignment of the amino acid sequence of the heavy chain of antibody 2.12.1fx (SEQ ID NO: 3) with that of germlne sequence DP-35 (3-11)/D3-3/JH6 (SEQ ID NO: 4). The sequence of antibody 2.12.1fx is shown above that for the germlne sequence. The signal sequences are in italics and the CDRs are underlined. The constant domain region begins with the amino acid residues ASTK and corresponds to amino acid residue 148 in the germlne and extends to the end of the sequence. The framework (FR) mutations are amino acid residues 21 and 116.

FIG. 4 shows an alignment of the amino acid sequence of the light chain of antibody 2.12.1fx (SEQ ID NO: 5) with that of germlne sequence A30/Jk1 (SEQ ID NO: 6). The sequence of antibody 2.12.1fx is shown above that for the germlne sequence. The signal sequences are in italics and the CDRs are underlined. The constant domains region begins with the amino acid residues TVAA and corresponds to amino acid residue 131 in the germlne and extends to the end of the sequence. The framework (FR) mutations are amino acid residues 43, 125, and 129.

FIG. 5 shows that anti-IGF-IR antibody 2.12.1fx inhibits IGF-I binding to 3T3-IGF-IR cells.

FIGS. 6A and 6B show the ability of antibody 2.12.1fx to block IGF-I mediated activation of IGF-IR as shown by decreased receptor-associated tyrosine phosphorylation (FIG. 6A) and the ability of antibody 2.12.1fx to induce the down regulation of IGF-1R on cells (FIG. 6B).

FIGS. 8A and 8B show that anti-IGF-IR antibody inhibits 3T3-IGF-IR tumor growth in vivo alone (FIG. 8A) or in combination with adriamycin (FIG. 8B).

DETAILED DESCRIPTION OF THE INVENTION

Figure 6A:
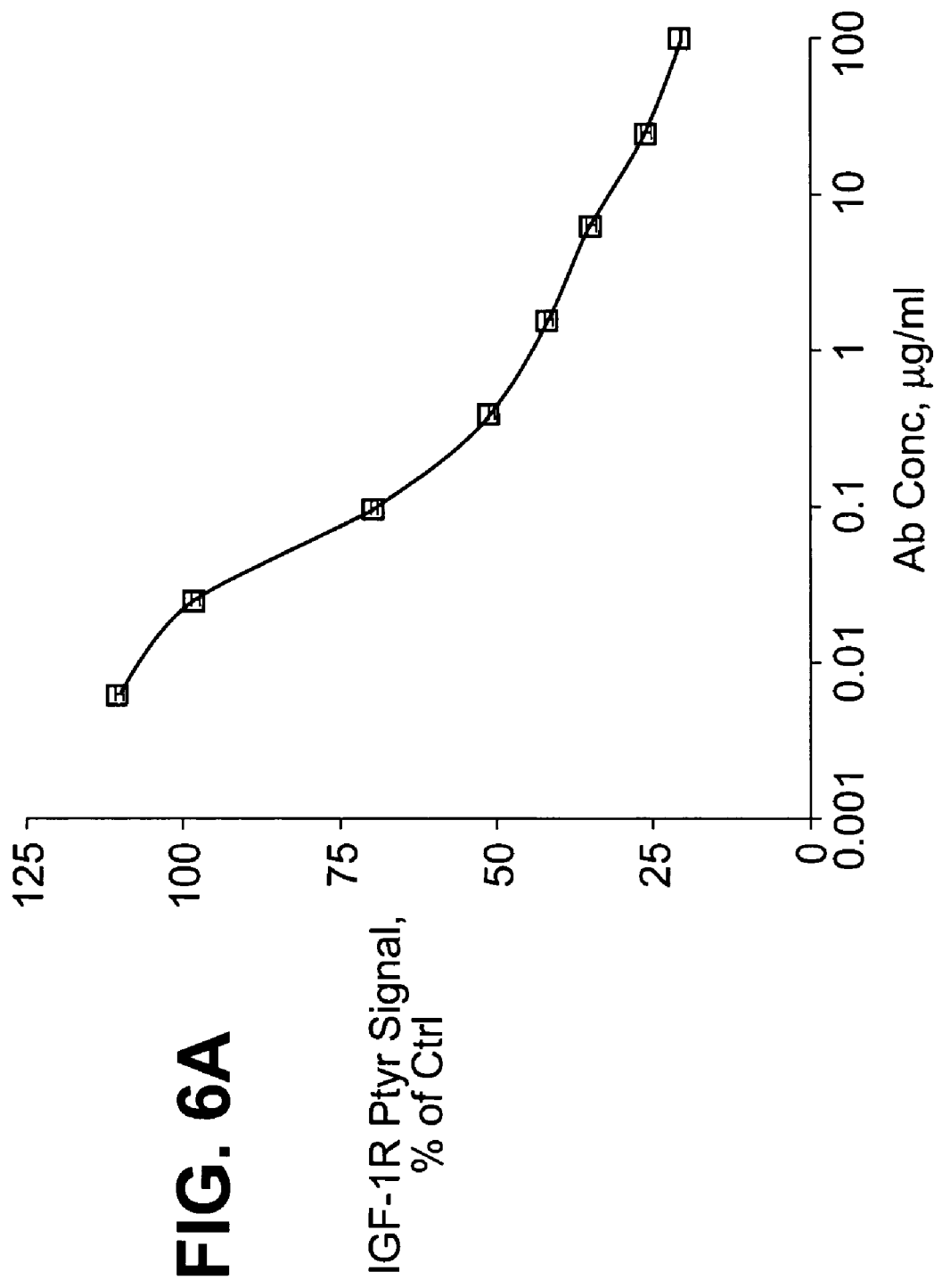

All patents, patent applications, and other references cited herein are hereby incorporated by reference in their entireties.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual,* 2d ed., Cold Spring Harbor Laboratory Press, Cold Spring Harbor, N.Y. (1989) and Ausubel et al., *Current Protocols in Molecular Biology,* Greene Publishing Associates (1992), and Harlow and Lane *Antibodies: A Laboratory Manual* Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation (1) is not associated with naturally associated components that accompany it in its native state, (2) is free of other proteins from the same species (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

A protein or polypeptide is "substantially pure," "substantially homogeneous" or "substantially purified" when at least about 60 to 75% of a sample exhibits a single species of polypeptide. The polypeptide or protein may be monomeric or multimeric. A substantially pure polypeptide or protein will typically comprise about 50%, 60, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide fragment" as used herein refers to a polypeptide that has an amino-terminal and/or carboxy-terminal deletion, but where the remaining amino acid sequence is identical to the corresponding positions in the naturally occurring sequence. Fragments typically are at least 5, 6, 8 or 10 amino acids long, preferably at least 14 amino acids long, more preferably at least 20 amino acids long, usually at least 50 amino acids long, even more preferably at least 70, 80, 90, 100, 150 or 200 amino acids long.

The term "polypeptide analog" as used herein refers to a polypeptide that is comprised of a segment of at least 25 amino acids that has substantial identity to a portion of an amino acid sequence and that has at least one of the following properties: (1) specific binding to IGF-IR under suitable binding conditions, (2) ability to block IGF-I or IGF-II binding to IGF-IR, or (3) ability to reduce IGF-IR cell surface expression or tyrosine phosphorylation in vitro or in vivo. Typically, polypeptide analogs comprise a conservative amino acid substitution (or insertion or deletion) with respect to the naturally occurring sequence. Analogs typically are at least 20 amino acids long, preferably at least 50, 60, 70, 80, 90, 100, 150 or 200 amino acids long or longer, and can often be as long as a full-length naturally-occurring polypeptide.

Non-peptide analogs are commonly used in the pharmaceutical industry as drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —$CH_2NH$—, —$CH_2S$—, —$CH_2$—$CH_2$—, —CH=CH-(cis and trans), —$COCH_2$—, —CH(OH)$CH_2$—, and —$CH_2SO$—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as κ and λ light chains. Heavy chains are classified as μ, Δ, γ, α, or ε, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminus to C-terminus, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

An "antibody" refers to an intact immunoglobulin. Antigen-binding portions may be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide.

An Fab fragment is a monovalent fragment consisting of the VL, VH, CL and CH I domains; a F(ab')$_2$ fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., *Nature* 341:544-546, 1989) consists of a VH domain.

A single-chain antibody (scFv) is an antibody in which a VL and VH regions are paired to form a monovalent molecules via a synthetic linker that enables them to be made as a single protein chain (Bird et al., Science 242: 423-426, 1988 and Huston et al., Proc. Natl. Acad. Sci. USA 85:5879-5883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., Proc. Natl. Acad. Sci. USA 90:6444-6448, 1993, and Poljak, R. J., et al., Structure 2:1121-1123, 1994). One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. Examples of isolated antibodies include an anti-IGF-IR antibody that has been affinity purified using IGF-IR is an isolated antibody, an anti-IGF-IR antibody that has been synthesized by a hybridoma or other cell line in vitro, and a human anti-IGF-IR antibody derived from a transgenic mouse.

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of ways, as described below.

A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In a preferred embodiment, one or more of the CDRs are derived from a human anti-IGF-IR antibody. In a more preferred embodiment, all of the CDRs are derived from a human anti-IGF-IR antibody. In another preferred embodiment, the CDRs from more than one human anti-IGF-IR antibodies are mixed and matched in a chimeric antibody. For instance, a chimeric antibody may comprise a CDR1 from the light chain of a first human anti-IGF-IR antibody may be combined with CDR2 and CDR3 from the light chain of a second human anti-IGF-IR antibody, and the CDRs from the heavy chain may be derived from a third anti-IGF-IR antibody. Further, the framework regions may be derived from one of the same anti-IGF-IR antibodies, from one or more different antibodies, such as a human antibody, or from a humanized antibody.

A "neutralizing antibody" or "an inhibitory antibody" is an antibody that. inhibits the binding of IGF-IR to IGF-I when an excess of the anti-IGF-IR antibody reduces the amount of IGF-I bound to IGF-IR by at least about 20%. In a preferred embodiment, the antibody reduces the amount of IGF-I bound to IGF-IR by at least 40%, more preferably 60%, even more preferably 80%, or even more preferably 85%. The binding reduction may be measured by any means known to one of ordinary skill in the art, for example, as measured in an in vitro competitive binding assay.

An "activating antibody" is an antibody that activates IGF-IR by at least about 20% when added to a cell, tissue or organism expressing IGF-IR. In a preferred embodiment, the antibody activates IGF-IR activity by at least 40%, more preferably 60%, even more preferably 80%, or even more preferably 85%. In a more preferred embodiment, the activating antibody is added in the presence of IGF-I or IGF-II. In another preferred embodiment, the activity of the activating antibody is measured by determining the amount of tyrosine autophosphorylation of IGF-IR.

Fragments or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991).

The term "surface plasmon resonance", as used herein, refers to an optical phenomenon that allows for the analysis of real-time biospecific interactions by detection of alterations in protein concentrations within a biosensor matrix, for example using the BlAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "$K_{off}$" refers to the off rate constant for dissociation of an antibody from the antibody/antigen complex.

The term "$K_d$" refers to the dissociation constant of a particular antibody-antigen interaction.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM, preferably $\leq 100$ nM and most preferably $\leq 10$ nM.

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "naturally occurring nucleotides" referred to herein include deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein A reference to a nucleic acid sequence encompasses its complement unless otherwise specified. Thus, a reference to a nucleic acid molecule having a particular sequence should be understood to encompass its complementary strand, with its complementary sequence.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "agent" is used herein to denote a chemical compound, a mixture of chemical compounds, a biological macromolecule, or an extract made from biological materials. The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

The antibody may be an IgG, an IgM, an IgE, an IgA or an IgD molecule. In a preferred embodiment, the antibody is an IgG and is an IgG1, IgG2, IgG3 or IgG4 subtype. In a more preferred embodiment, the anti-IGF-IR antibody is subclass IgG2.

The class and subclass of anti-IGF-IR antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

The invention also provides an anti-IGF-IR antibody that comprises variable sequences encoded by a human κ gene. In a preferred embodiment, the variable sequences are encoded by either the Vκ A27, A30 or O12 gene family. In a preferred embodiment, the variable sequences are encoded by a human Vκ A30 gene. In a more preferred embodiment, the light chain comprises three framework mutation reverted back to an amino acid sequence encoded by the germline sequence.

SEQ ID NO 1 provides the DNA sequence of the heavy chain of 2.12.1fx. SEQ ID NO 2 provides the DNA sequence of the light chain of 2.12.1fx. SEQ ID NO 3 provides the amino acid sequence of the heavy chain of 2.12.1fx. SEQ ID NO 4 provides the amino acid sequence of germlne DP-35. SEQ ID NO 5 provides the amino acid sequence of the light chain of 2.12.1fx and SEQ ID NO 6 provides the amino acid sequence of germlne A30/Jk1. The sequences shown are for the immature precursors to the antibodies that include a signal sequence.

In one embodiment, the anti-IGF-IR antibody comprises variable region sequences encoded by the human $V_H$ DP-35, DP-47, DP-70, DP-71 or VIV-4/4.35 gene family. In a preferred embodiment, the variable region sequence is derived from a human $V_H$ DP-35 gene. In a more preferred embodiment, the heavy chain comprises two framework mutations reverted back to the amino acid sequence encoded by the germlne sequence.

Nucleic acid molecules encoding the anti-IGF-IR antibody of the invention are provided. In one embodiment, the nucleic acid molecule encodes a heavy and/or light chain of an anti-IGF-IR immunoglobulin. In a preferred embodiment, a single nucleic acid molecule encodes a heavy chain of an anti-IGF-IR immunoglobulin and another nucleic acid molecule encodes the light chain of an anti-IGF-IR immunoglobulin. In a more preferred embodiment, the encoded immunoglobulin is a human immunoglobulin, preferably a human IgG. The encoded light chain may be a λ chain or a κ chain, preferably a κ chain.

In one embodiment, the nucleic acid molecule encoding the variable region of the light chain is derived from the A30, A27 or O12 Vκ gene. In a preferred embodiment, the light chain is derived from the A30 Vκ gene. In another preferred embodiment, the nucleic acid molecule encoding the light chain comprises the joining region derived from Jκ1, Jκ2 or Jκ4.

The invention also provides a nucleic acid molecule comprising a nucleic acid sequence that encodes the amino acid sequence of the variable region of the light chain of 2.12.1fx.

The invention also provides a nucleic acid molecule encoding the variable region of the heavy chain (VH) that is derived from the DP-35, DP-47, DP-71 or VIV-4/4.35 VH gene, preferably the DP-35 VH gene. In another preferred embodiment, the nucleic acid molecule encoding the VH comprises the joining region derived from JH6 or JH5, more preferably JH6. The invention also provides a nucleic acid molecule comprising a nucleic acid sequence that encodes the amino acid sequence of the variable region of the heavy chain of 2.12.1fx.

The nucleic acid molecule encoding either or both of the entire heavy and light chains of a human antibody or the variable regions thereof may be obtained from any source that produces a human antibody. Methods of isolating mRNA encoding an antibody are well-known in the art. See, e.g., Sambrook et al. The mRNA may be used to produce cDNA for use in the polymerase chain reaction (PCR) or cDNA cloning of antibody genes. In one embodiment of the invention, the nucleic acid molecules may be obtained from a hybridoma that expresses an anti-IGF-IR antibody, as described above, preferably a hybridoma that has as one of its fusion partners a transgenic animal cell that expresses human immunoglobulin genes, such as a XENOMOUSE™, non-human mouse transgenic animal or a non-human, non-mouse transgenic animal. IGF-1R antibodies may apply generally to human antibodies of the invention other than those specific to IGF-1R.

A nucleic acid molecule encoding the entire heavy chain of an anti-IGF-IR antibody may be constructed by fusing a nucleic acid molecule encoding the variable domain of a heavy chain or an antigen-binding domain thereof with a constant domain of a heavy chain. Similarly, a nucleic acid molecule encoding the light chain of an anti-IGF-IR antibody may be constructed by fusing a nucleic acid molecule encoding the variable domain of a light chain or an antigen-binding domain thereof with a constant domain of a light chain. The nucleic acid molecules encoding the VH and VL chain may be converted to full-length antibody genes by inserting them into expression vectors already encoding heavy chain constant and light chain constant regions, respectively, such that the VH segment is operatively linked to the heavy chain constant region (CH) segment(s) within the vector and the VL segment is operatively linked to the light chain constant region (CL) segment within the vector. Alternatively, the nucleic acid molecules encoding the VH or VL chains are converted into full-length antibody genes by linking, e.g., ligating, the nucleic acid molecule encoding a VH chain to a nucleic acid molecule encoding a CH chain using standard molecular biological techniques. The same may be achieved using nucleic acid molecules encoding VL and CL chains. The sequences of human heavy and light chain constant region genes are known in the art. See, e.g., Kabat et al., *Sequences of Proteins of Immunological Interest,* 5th Ed., NIH Publ. No. 91-3242, 1991. Nucleic acid molecules encoding the full-length heavy and/or light chains may then be expressed from a cell into which they have been introduced and the anti-IGF-IR antibody isolated.

In another embodiment, a nucleic acid molecule encoding either the heavy chain of an anti-IGF-IR antibody or an antigen-binding domain thereof, or the light chain of an anti-IGF-IR antibody or an antigen-binding domain thereof may be isolated from a non-human, non-mouse animal that expresses human immunoglobulin genes and has been immunized with an IGF-IR antigen. In other embodiment, the nucleic acid molecule may be isolated from an anti-IGF-IR antibody-producing cell derived from a non-transgenic animal or from a human patient who produces anti-IGF-IR antibodies. Methods of isolating mRNA from the anti-IGF-IR antibody-producing cells may be isolated by standard techniques, cloned and/or amplified using PCR and library construction techniques, and screened using standard protocols to obtain nucleic acid molecules encoding anti-IGF-IR heavy and light chains.

The nucleic acid molecules may be used to recombinantly express large quantities of anti-IGF-IR antibodies, as described below. The nucleic acid molecules may also be used to produce single chain antibodies, immunoadhesins, diabodies, mutated antibodies and antibody derivatives, as described further below.

In another embodiment, the nucleic acid molecules of the invention may be used as probes or PCR primers for specific antibody sequences. For instance, a nucleic acid molecule probe may be used in diagnostic methods or a nucleic acid molecule PCR primer may be used to amplify regions of DNA that could be used, inter alia, to isolate nucleic acid sequences for use in producing variable domains of anti-IGF-IR antibodies. In a preferred embodiment, the nucleic acid molecules are oligonucleotides. In a more preferred embodiment, the oligonucleotides are from highly variable regions of the heavy and light chains of the antibody of interest.

The invention provides vectors comprising the nucleic acid molecules of the invention that encode the heavy chain or the antigen-binding portion thereof. The invention also provides vectors comprising the nucleic acid molecules of the invention that encode the light chain or antigen-binding portion thereof. The invention also provides vectors comprising nucleic acid molecules encoding fusion proteins, modified antibodies, antibody fragments, and probes thereof.

To express the antibodies, or antibody portions of the invention, DNAs encoding partial or full-length light and heavy chains, obtained as described above, are inserted into expression vectors such that the genes are operatively linked to transcriptional and translational control sequences. Expression vectors include plasmids, retroviruses, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr- host cells with methotrexate selection/amplification) and the neo gene (for G418 selection).

Nucleic acid molecules encoding the heavy chain or an antigen-binding portion thereof and/or the light chain or an antigen-binding portion thereof of an anti-IGF-IR antibody of the invention, and vectors comprising these nucleic acid molecules, can be used for transformation of a suitable host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, e.g., U.S. Patent Nos. 4,399,216, 4,912,040, 4,740,461, and 4,959,455 (which patents are hereby incorporated herein by reference).

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

The invention also provides transgenic non-human animals comprising one or more nucleic acid molecules of the invention that may be used to produce antibodies of the invention. Antibodies can be produced in and recovered from tissue or bodily fluids, such as milk, blood or urine, of goats, cows, horses, pigs, rats, mice, rabbits, hamsters or other mammals. See, e.g., U.S. Pat. Nos. 5,827,690, 5,756,687, 5,750,172, and 5,741,957. As described above, non-human transgenic animals that comprise human immunoglobulin loci can be produced by immunizing with IGF-IR or a portion thereof.

In another embodiment, non-human transgenic animals are produced by introducing one or more nucleic acid molecules of the invention into the animal by standard transgenic techniques. See Hogan, supra. The transgenic cells used for making the transgenic animal can be embryonic stem cells or somatic cells. The transgenic non-human organisms can be chimeric, nonchimeric heterozygotes, and nonchimeric homozygotes. See, e.g., Hogan et al., *Manipulating the Mouse Embryo: A Laboratory Manual* 2ed., Cold Spring Harbor Press (1999); Jackson et al., *Mose Genetics and Transgenics: A Practical Approach*, Oxford University Press (2000); and Pinkert, *Transgenic Animal Technology: A Laboratory Handbook*, Academic Press (1999). In another embodiment, the transgenic non-human organisms may have a targeted disruption and replacement that encodes a heavy chain and/or a light chain of interest. In a preferred embodiment, the transgenic animals comprise and express nucleic acid molecules encoding heavy and light chains that bind specifically to IGF-IR, preferably human IGF-IR. In another embodiment, the transgenic animals comprise nucleic acid molecules encoding a modified antibody such as a single-chain antibody, a chimeric antibody or a humanized antibody. The anti-IGF-IR antibodies may be made in any transgenic animal. In a preferred embodiment, the non-human animals are mice, rats, sheep, pigs, goats, cattle or horses. The non-human transgenic animal expresses said encoded polypeptides in blood, milk, urine, saliva, tears, mucus and other bodily fluids.

Recombinant anti-IGF-IR human antibodies in addition to the anti-IGF-IR antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum. Antibod. Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nuc Acid Res 19:4133-4137; and Barbas et al. (1991) Proc. Natl. Acad. Sci. USA 88:7978-7982.

In a preferred embodiment, to isolate human anti-IGF-IR antibodies with the desired characteristics, a human anti-IGF-IR antibody as described herein is first used to select human heavy and light chain sequences having similar binding activity toward IGF-IR, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., Nature (1990) 348:552-554;

and Griffiths et al., (1993) EMBO J 12:725-734. The scFv antibody libraries preferably are screened using human IGF-IR as the antigen.

Once initial human VL and VH segments are selected, "mix and match" experiments, in which different pairs of the initially selected VL and VH segments are screened for IGF-IR binding, are performed to select preferred VL/VH pair combinations. Additionally, to further improve the quality of the antibody, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to IGF-IR.

Following screening and isolation of an anti-IGF-IR antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express a recombinant human antibody isolated by screening of a combinatorial library, the DNA encoding the antibody is cloned into a recombinant expression vector and introduced into a mammalian host cells, as described above.

The class of an anti-IGF-IR antibody obtained as described above may be switched with another. In one aspect of the invention, a nucleic acid molecule encoding VL or VH is isolated using methods well-known in the art such that it does not include any nucleic acid sequences encoding CL or CH. The nucleic acid molecule encoding VL or VH are then operatively linked to a nucleic acid sequence encoding a CL or CH from a different class of immunoglobulin molecule. This may be achieved using a vector or nucleic acid molecule that comprises a CL or CH chain, as described above. For example, an anti-IGF-IR antibody that was originally IgM may be class switched to an IgG. Further, the class switching may be used to convert one IgG subclass to another, e.g., from IgG1 to IgG2. A preferred method for producing an antibody of the invention comprising a desired isotypes comprises the steps of isolating a nucleic acid encoding the heavy chain of an anti-IGF-IR antibody and a nucleic acid encoding the light chain of an anti-IGF-IR antibody, obtaining the variable region of the heavy chain, ligating the variable region of the heavy chain with the constant domain of a heavy chain of the desired isotype, expressing the light chain and the ligated heavy chain in a cell, and collecting the anti-IGF-IR antibody with the desired isotype.

One may use the nucleic acid molecules described above to generate antibody derivatives using techniques and methods known to one of ordinary skill in the art. According to the invention, one or more mutated amino acid residues at selected position(s) are then replaced with a corresponding germ line residue.

In another embodiment, a fusion antibody or immunoadhesin may be made which comprises all or a portion of an anti-IGF-IR antibody linked to another polypeptide. In a preferred embodiment, only the variable regions of the anti-IGF-IR antibody are linked to the polypeptide. In another preferred embodiment, the VH domain of an anti-IGF-IR antibody are linked to a first polypeptide, while the VL domain of an anti-IGF-IR antibody are linked to a second polypeptide that associates with the first polypeptide in a manner in which the VH and VL domains can interact with one another to form an antibody binding site. In another preferred embodiment, the VH domain is separated from the VL domain by a linker such that the VH and VL domains can interact with one another. The VH-linker-VL antibody is then linked to the polypeptide of interest. The fusion antibody is useful to directing a polypeptide to an IGF-IR-expressing cell or tissue. The polypeptide may be a therapeutic agent, such as a toxin, growth factor or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody, (scFv) the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554). The single chain antibody may be monovalent, if only a single VH and VL are used, bivalent, if two VH and VL are used, or polyvalent, if more than two VH and VL are used.

In another embodiment, other modified antibodies may be prepared using anti-IGF-IR-encoding nucleic acid molecules. For instance, "Kappa bodies" (III et al., *Protein Eng* 10: 949-57 (1997)), "Minibodies" (Martin et al., *EMBO J* 13: 5303-9 (1994)), "Diabodies" (Holliger et al., *PNAS USA* 90: 6444-6448 (1993)), or "Janusins" (Traunecker et al., *EMBO J* 10: 3655-3659 (1991) and Traunecker et al. "Janusin: new molecular design for bispecific reagents" *Int J Cancer Suppl* 7:51-52 (1992)) may be prepared using standard molecular biological techniques following the teachings of the specification.

An antibody or antibody portion of the invention can be derivatized or linked to another molecule (e.g., another peptide or protein). In general, the antibodies or portion thereof is derivatized such that the IGF-IR binding is not affected adversely by the derivatization or labeling. Accordingly, the antibodies and antibody portions of the invention are intended to include both intact and modified forms of the human anti-IGF-IR antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another type of derivatized antibody is a labeled antibody. Useful detection agents with which an antibody or antibody portion of the invention may be derivatized include fluorescent compounds, including fluorescein, fluorescein isothiocyanate, rhodamine, 5-dimethylamine-1-napthalenesulfonyl chloride, phycoerythrin, lanthanide phosphors and the like. An antibody may also be labeled with enzymes that are useful for detection, such as horseradish peroxidase, β-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody may also be labeled with biotin, and detected through indirect measurement of avidin or streptavidin binding. An antibody may be labeled with a magnetic agent, such as gadolinium. An antibody may also be labeled with a predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

An anti-IGF-IR antibody may also be labeled with a radiolabeled amino acid. The radiolabel may be used for both diagnostic and therapeutic purposes. For instance, the radiolabel may be used to detect IGF-IR-expressing tumors by x-ray or other diagnostic techniques. Further, the radiolabel may be used therapeutically as a toxin for cancerous cells or tumors. Examples of labels for polypeptides include, but are not limited to, the following radioisotopes or radionuclides—$^{3}H$, $^{14}C$, $^{15}N$, $^{35}S$, $^{90}Y$, $^{99}Tc$, $^{111}In$, $^{125}I$, $^{131}I$.

An anti-IGF-IR antibody may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding.

The invention also relates to a pharmaceutical composition for the treatment of a hyperproliferative disorder in a mammal which comprises a therapeutically effective amount of a compound of the invention and a pharmaceutically acceptable carrier. In one embodiment, said pharmaceutical composition is for the treatment of cancer such as brain, lung, squamous cell, bladder, gastric, pancreatic, breast, head, neck, renal, kidney, ovarian, prostate, colorectal, esophageal, gynecological or thyroid cancer. Patients that can be treated with a compound of the invention according to the methods of this invention include, for example, patients that have been diagnosed as having multiple myeloma, liquid tumor, liver cancer, thymus disorder, T-cell mediated auto-immune disease, endocronological disorder, ischemia, neurodegenerative disorder, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

In another embodiment, said pharmaceutical composition relates to non-cancerous hyperproliferative disorders such as, without limitation, restenosis after angioplasty and psoriasis. In another embodiment, the invention relates to pharmaceutical compositions for the treatment of a mammal that requires activation of IGF-IR, wherein the pharmaceutical composition comprises a therapeutically effective amount of an activating antibody of the invention and a pharmaceutically acceptable carrier. Pharmaceutical compositions comprising activating antibodies may be used to treat animals that lack sufficient IGF-I or IGF-II, or may be used to treat osteoporosis, frailty or disorders in which the mammal secretes too little active growth hormone or is unable to respond to growth hormone.

The anti-IGF-IR antibody of the invention can be incorporated into pharmaceutical compositions suitable for administration to a subject. Typically, the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-IGF-IR antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody of the present invention can be administered by a variety of methods known in the art, although for many therapeutic applications, the preferred route/mode of administration is intraperitoneal, subcutaneous, intramuscular, intravenous or infusion. As will be appreciated by the skilled artisan, the route and/or mode of administration will vary depending upon the desired results. In one embodiment, the antibody of the present invention can be administered as a single dose or may be administered as multiple doses.

In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Supplementary active compounds can also be incorporated into the composition. In certain embodiments, an anti-IGF-IR antibody of the invention is coformulated with and/or coadministered with one or more additional therapeutic agents, such as a chemotherapeutic agent, an antineoplastic agent or an anti-tumor agent. For example, an anti-IGF-IR antibody may be coformulated and/or coadministered with one or more additional therapeutic agents. These agents include, without limitation, antibodies that bind other targets (e.g., antibodies that bind one or more growth factors or cytokines, their cell surface receptors or IGF-I), IGF-I binding proteins, antineoplastic agents, chemotherapeutic agents, anti-tumor agents, antisense oligonucleotides against IGF-IR or IGF-I, peptide analogues that block IGF-IR activation, soluble IGF-IR, and/or one or more chemical agents that inhibit IGF-I production or activity, which are known in the art, e.g., octreotide. For a pharmaceutical composition comprising an activating antibody, the anti-IGF-IR antibody may be formulated with a factor that increases cell proliferation or prevents apoptosis. Such factors include growth factors such as IGF-I, and/or analogues of IGF-I that activate IGF-IR. Such combination therapies may require lower dosages of the anti-IGF-IR antibody as well as the co-administered agents, thus avoiding possible toxicities or complications associated with the various monotherapies. In one embodiment, the antibody and one or more additional therapeutic agent.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. Pharmaceutical composition comprising the antibody or comprising a combination therapy comprising the antibody and one or more additional therapeutic agents may be formulated for single or multiple doses. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals. A particularly useful formulation is 5 mg/ml anti-IGF-IR antibody in a buffer of 20 mM sodium citrate, pH 5.5, 140 mM NaCl, and 0.2 mg/ml polysorbate 80.

An exemplary, non-limiting range for a therapeutically or prophylactically effective amount of an antibody or antibody portion of the invention is 0.1-100 mg/kg, more preferably 0.5-50 mg/kg, more preferably 1-20 mg/kg, and even more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. In one embodiment, the therapeutically or prophylactically effective amount of an antibody or antigen-binding portion thereof is administered along with one or more additional therapeutic agents.

In another aspect, the invention relates to administration of an anti-IGF-IR antibody of the invention for the treatment of cancer in a dose of less than 300 mg per month.

Another aspect of the present invention provides kits comprising the anti-IGF-IR antibodies and the pharmaceutical compositions comprising these antibodies. A kit may include, in addition to the antibody or pharmaceutical composition, diagnostic or therapeutic agents. A kit may also include instructions for use in a diagnostic or therapeutic method. In a preferred embodiment, the kit includes the antibody or a pharmaceutical composition thereof and a diagnostic agent that can be used in a method described below. In another preferred embodiment, the kit includes the antibody or a pharmaceutical composition thereof and one or more therapeutic agents, such as an additional antineoplastic agent, anti-tumor agent or chemotherapeutic agent, that can be used in a method described below.

This invention also relates to pharmaceutical compositions for inhibiting abnormal cell growth in a mammal which comprise an amount of a compound of the invention in combination with an amount of a chemotherapeutic agent, wherein the amounts of the compound, salt, solvate, or prodrug, and of the chemotherapeutic agent are together effective in inhibiting abnormal cell growth. Many chemotherapeutic agents are presently known in the art. In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of the invention. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP inhibitors are those that do not demonstrate arthralgia. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, RS 13-0830, and the compounds recited in the following list: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R, 3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R, 3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-icyclo[3.2.1]octane-3-carboxylic acid hydroxyamide; 3-endo-3-[4-(4-fluoro-phenoxy)-benzenesulfonylamino]-8-oxa-icyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

A compound of the invention can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc.). EGF-R inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), Cl-1033 (Warner Lambert Parke Davis), Cl-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGF-R Vaccine (York Medical/Centro de Immunologia Molecular (CIM)). These and other EGF-R-inhibiting agents can be used in the present invention.

VEGF inhibitors, for example SU-5416 and SU-6668 (Sugen Inc.), SH-268 (Schering), and NX-1838 (NeXstar) can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov.

10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc.); anti-VEGF monoclonal antibody of Genentech, Inc.; and angiozyme, a synthetic ribozyme from Ribozyme and Chiron. These and other VEGF inhibitors can be used in the present invention as described herein.

ErbB2 receptor inhibitors, such as GW-282974 (Glaxo Wellcome pic), and the monoclonal antibodies AR-209 (Aronex Pharmaceuticals Inc.) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

The anti-IGF-IR antibody may be used to detect IGF-IR in a biological sample in vitro or in vivo. The anti-IGF-IR antibody may be used in a conventional immunoassay, including, without limitation, an ELISA, an RIA, FACS, tissue immunohistochemistry, Western blot or immunoprecipitation. The anti-IGF-IR antibody of the invention may be used to detect IGF-IR from humans. In another embodiment, the anti-IGF-IR antibody may be used to detect IGF-IR from Old World primates such as cynomolgus and rhesus monkeys, chimpanzees and apes. The invention provides a method for detecting anti-IGF-IR in a biological sample comprising contacting a biological sample with an anti-IGF-IR antibody of the invention and detecting the bound antibody bound to anti-IGF-IR, to detect the IGF-IR in the biological sample. In one embodiment, the anti-IGF-IR antibody is directly labeled with a detectable label. In another embodiment, the anti-IGF-IR antibody (the first antibody) is unlabeled and a second antibody or other molecule that can bind the anti-IGF-IR antibody is labeled. As is well known to one of skill in the art, a second antibody is chosen that is able to specifically bind the specific species and class of the first antibody. For example, if the anti-IGF-IR antibody is a human IgG, then the secondary antibody may be an anti-human-lgG. Other molecules that can bind to antibodies include, without limitation, Protein A and Protein G, both of which are available commercially, e.g., from Pierce Chemical Co.

Suitable labels for the antibody or secondary have been disclosed supra, and include various enzymes, prosthetic groups, fluorescent materials, luminescent materials, magnetic agents and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; an example of a magnetic agent includes gadolinium; and examples of suitable radioactive material include $^{125}I$, $^{131}I$, $^{35}S$ or $^{3}H$.

In an alternative embodiment, IGF-IR can be assayed in a biological sample by a competition immunoassay utilizing IGF-IR standards labeled with a detectable substance and an unlabeled anti-IGF-IR antibody. In this assay, the biological sample, the labeled IGF-IR standards and the anti-IGF-IR antibody are combined and the amount of labeled IGF-IR standard bound to the unlabeled antibody is determined. The amount of IGF-IR in the biological sample is inversely proportional to the amount of labeled IGF-IR standard bound to the anti-IGF-IR antibody.

One may use the immunoassays disclosed above for a number of purposes. In one embodiment, the anti-IGF-IR antibody may be used to detect IGF-IR in cells in cell culture. In a preferred embodiment, the anti-IGF-IR antibody may be used to determine the level of tyrosine phosphorylation, tyrosine autophosphorylation of IGF-IR, and/or the amount of IGF-IR on the cell surface after treatment of the cells with various compounds. This method can be used to test compounds that may be used to activate or inhibit IGF-IR. In this method, one sample of cells is treated with a test compound for a period of time while another sample is left untreated. If tyrosine autophosphorylation is to be measured, the cells are lysed and tyrosine phosphorylation of the IGF-IR is measured using an immunoassay described above or as described previously using an ELISA. If the total level of IGF-IR is to be measured, the cells are lysed and the total IGF-IR level is measured using one of the immunoassays described above.

A preferred immunoassay for determining IGF-IR tyrosine phosphorylation or for measuring total IGF-IR levels is an ELISA or Western blot. If only the cell surface level of IGF-IR is to be measured, the cells are not lysed, and the cell surface levels of IGF-IR are measured using one of the immunoassays described above. A preferred immunoassay for determining cell surface levels of IGF-IR includes the steps of labeling the cell surface proteins with a detectable label, such as biotin or $^{125}I$, immunoprecipitating the IGF-IR with an anti-IGF-IR antibody and then detecting the labeled IGF-IR. Another preferred immunoassay for determining the localization of IGF-IR, e.g., cell surface levels, is by using immunohistochemistry. Methods such as ELISA, RIA, Western blot, immunohistochemistry, cell surface labeling of integral membrane proteins and immunoprecipitation are well known in the art. See, e.g., Harlow and Lane, supra. In addition, the immunoassays may be scaled up for high throughput screening in order to test a large number of compounds for either activation or inhibition of IGF-IR.

The anti-IGF-IR antibody of the invention may also be used to determine the levels of IGF-IR in a tissue or in cells derived from the tissue. In a preferred embodiment, the tissue is a diseased tissue. In a more preferred embodiment, the tissue is a tumor or a biopsy thereof. In a preferred embodiment of the method, a tissue or a biopsy thereof is excised from a patient. The tissue or biopsy is then used in an immunoassay to determine, e.g., IGF-IR levels, cell surface levels of IGF-IR, levels of tyrosine phosphorylation of IGF-IR, or localization of IGF-IR by the methods discussed above. The method can be used to determine if a tumor expresses IGF-IR at a high level.

The above-described diagnostic method can be used to determine whether a tumor expresses high levels of IGF-IR, which may be indicative that the tumor will respond well to treatment with anti-IGF-IR antibody. The diagnostic method may also be used to determine whether a tumor is potentially cancerous, if it expresses high levels of IGF-IR, or benign, if it expresses low levels of IGF-IR. Further, the diagnostic method may also be used to determine whether treatment with anti-IGF-IR antibody (see below) is causing a tumor to express lower levels of IGF-IR and/or to express lower levels of tyrosine autophosphorylation, and thus can be used to determine whether the treatment is successful. In general, a method to determine whether an anti-IGF-IR antibody decreases tyrosine phosphorylation comprises the steps of measuring the level of tyrosine phosphorylation in a cell or tissue of interest, incubating the cell or tissue with an anti-IGF-IR antibody or antigen-binding portion thereof, then re-measuring the level of tyrosine phosphorylation in the cell or tissue. The tyrosine phosphorylation of IGF-IR or of another protein(s) may be measured. The diagnostic method may also be used to determine whether a tissue or cell is not expressing high enough levels of IGF-IR or high enough levels of activated IGF-IR, which may be the case for individuals with dwarfism, osteoporosis or diabetes. A diagnosis that levels of IGF-IR or active IGF-IR are too low could be used for treatment with activating anti-IGF-IR antibodies, IGF-I or other therapeutic agents for increasing IGF-IR levels or activity.

Based on the ability of the antibody of the present invention to down regulate IGF-1R on peripheral lymphocytes, a "biomarker strategy" can be employed to monitor the expression of IGF-1R on circulating tumor and/or normal cells from patients treated with the antibody of the invention. Other antibodies, such as antibodies described in WO 02/05359, published Jul. 11, 2002 can also be used. These cells can include but are not limited to CD19+ cells, and may also include all white blood cells such as monocytes, granulocytes, and lymphocytes.

The antibody of the present invention may also be used in vivo to localize tissues and organs that express IGF-IR. In a preferred embodiment, the anti-IGF-IR antibody can be used to localize IGF-IR-expressing tumors. The method comprises the steps of administering an anti-IGF-IR antibody or a pharmaceutical composition thereof to a patient in need of such a diagnostic test and subjecting the patient to imaging analysis determine the location of the IGF-IR-expressing tissues. Imaging analysis is well known in the medical art, and includes, without limitation, x-ray analysis, magnetic resonance imaging (MRI) or computed tomography (CE). In another embodiment of the method, a biopsy is obtained from the patient to determine whether the tissue of interest expresses IGF-IR rather than subjecting the patient to imaging analysis. In a preferred embodiment, the anti-IGF-IR antibody may be labeled with a detectable agent that can be imaged in a patient. For example, the antibody may be labeled with a contrast agent, such as barium, which can be used for x-ray analysis, or a magnetic contrast agent, such as a gadolinium chelate, which can be used for MRI or CE. Other labeling agents include, without limitation, radioisotopes, such as $^{99}$Tc. In another embodiment, the anti-IGF-IR antibody will be unlabeled and will be imaged by administering a second antibody or other molecule that is detectable and that can bind the anti-IGF-IR antibody.

In another embodiment, the invention provides a method for inhibiting IGF-IR activity by administering an anti-IGF-IR antibody of the invention to a patient in need thereof. The antibody of the present invention may be used therapeutically. In another preferred embodiment, the IGF-IR is human and the patient is a human patient. Alternatively, the patient may be a mammal that expresses an IGF-IR that the anti-IGF-IR antibody cross-reacts with. The antibody may be administered to a non-human mammal expressing an IGF-IR with which the antibody cross-reacts (i.e. a primate, or a cynomolgus or rhesus monkey) for veterinary purposes or as an animal model of human disease. Such animal models may be useful for evaluating the therapeutic efficacy of antibodies of this invention.

As used herein, the term "a disorder in which IGF-IR activity is detrimental" is intended to include diseases and other disorders in which the presence of high levels of IGF-IR in a subject suffering from the disorder has been shown to be or is suspected of being either responsible for the pathophysiology of the disorder or a factor that contributes to a worsening of the disorder. Accordingly, a disorder in which high levels of IGF-IR activity is detrimental is a disorder in which inhibition of IGF-IR activity is expected to alleviate the symptoms and/or progression of the disorder. Such disorders may be evidenced, for example, by an increase in the levels of IGF-IR on the cell surface or in increased tyrosine autophosphorylation of IGF-IR in the affected cells or tissues of a subject suffering from the disorder. The increase in IGF-IR levels may be detected, for example, using an anti-IGF-IR antibody as described above.

In a preferred embodiment, an anti-IGF-IR antibody may be administered to a patient who has an IGF-IR-expressing tumor. A tumor may be a solid tumor or may be a non-solid tumor, such as a lymphoma. In a more preferred embodiment, an anti-IGF-IR antibody may be administered to a patient who has an IGF-IR-expressing tumor that is cancerous. In an even more preferred embodiment, the anti-IGF-IR antibody is administered to a patient who has a tumor of the lung, breast, prostate or colon. In a highly preferred embodiment, the method causes the tumor not to increase in weight or volume or to decrease in weight or volume. In another embodiment, the method causes the IGF-IR on the tumor to be internalized. In a preferred embodiment, the antibody is 2.12.1fx, or comprises a heavy chain, light chain or antigen-binding region thereof.

In another preferred embodiment, an anti-IGF-IR antibody may be administered to a patient who expresses inappropriately high levels of IGF-1. It is known in the art that high-level expression of IGF-I can lead to a variety of common cancers. In a more preferred embodiment, the anti-IGF-IR antibody is administered to a patient with prostate cancer, glioma or fibrosarcoma. In an even more preferred embodiment, the method causes the cancer to stop proliferating abnormally, or not to increase in weight or volume or to decrease in weight or volume.

In one embodiment, said method relates to the treatment of cancer such as brain, squamous cell, bladder, gastric, pancreatic, breast, head, neck, esophageal, prostate, colorectal, lung, renal, kidney, ovarian, gynecological or thyroid cancer. Patients that can be treated with a compound of the invention according to the methods of this invention include, for example, patients that have been diagnosed as having multiple myeloma, liquid tumor, liver cancer, thymus disorder, T-cell mediated auto-immune disease, endocronological disorder, ischemia, neurodegenerative disorder, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

The antibody may be administered once, but more preferably is administered multiple times. The antibody may be administered from three times daily to once every six months. The administering may be on a schedule such as three times daily, twice daily, once daily, once every two days, once every three days, once weekly, once every two weeks, once every month, once every two months, once every three months and once every six months. The antibody may be administered via an oral, mucosal, buccal, intranasal, inhalable, intravenous, subcutaneous, intramuscular, parenteral, intratumor or topical route. The antibody may be administered at a site distant from the site of the tumor. The antibody may also be administered continuously via a minipump. The antibody may be administered once, at least twice or for at least the period of time until the condition is treated, palliated or cured. The antibody generally will be administered for as long as the tumor is present provided that the antibody causes the tumor or cancer to stop growing or to decrease in weight or volume. The antibody will generally be administered as part of a pharmaceutical composition as described supra. The dosage of antibody will generally be in the range of 0.1-100 mg/kg, more preferably 0.5-50 mg/kg, more preferably 1-20 mg/kg, and even more preferably 1-10 mg/kg. The serum concentration of the antibody may be measured by any method known in the art. The antibody may also be administered prophylactically in order to prevent a cancer or tumor from occurring. This may be especially useful in patients that have a "high normal" level of IGF-I because these patients have been shown to have a higher risk of developing common cancers. See Rosen et al., supra.

In another aspect, the anti-IGF-IR antibody may be co-administered with other therapeutic agents, such as antineoplastic drugs or molecules, to a patient who has a hyperproliferative disorder, such as cancer or a tumor. In one aspect, the invention relates to a method for the treatment of the hyperproliferative disorder in a mammal comprising administering to said mammal a therapeutically effective amount of a compound of the invention in combination with an anti-tumor agent selected from the group consisting of, but not limited to, mitotic inhibitors, alkylating agents, anti-metabolites, intercalating agents, growth factor inhibitors, cell cycle inhibitors, enzymes, topoisomerase inhibitors, biological response modifiers, anti-hormones, kinase inhibitors, matrix metalloprotease inhibitors, genetic therapeutics and anti-androgens. In a more preferred embodiment, the antibody may be administered with an antineoplastic agent, such as adriamycin or taxol. In another preferred embodiment, the antibody or combination therapy is administered along with radiotherapy, chemotherapy, photodynamic therapy, surgery or other immunotherapy. In yet another preferred embodiment, the antibody will be administered with another antibody. For example, the anti-IGF-IR antibody may be administered with an antibody or other agent that is known to inhibit tumor or cancer cell proliferation, e.g., an antibody or agent that inhibits erbB2 receptor, EGF-R, CD20 or VEGF.

Co-administration of the antibody with an additional therapeutic agent (combination therapy) encompasses administering a pharmaceutical composition comprising the anti-IGF-IR antibody and the additional therapeutic agent and administering two or more separate pharmaceutical compositions, one comprising the anti-IGF-IR antibody and the other(s) comprising the additional therapeutic agent(s). Further, although co-administration or combination therapy generally means that the antibody and additional therapeutic agents are administered at the same time as one another, it also encompasses instances in which the antibody and additional therapeutic agents are administered at different times. For instance, the antibody may be administered once every three days, while the additional therapeutic agent is administered once daily. Alternatively, the antibody may be administered prior to or subsequent to treatment of the disorder with the additional therapeutic agent. Similarly, administration of the anti-IGF-IR antibody may be administered prior to or subsequent to other therapy, such as radiotherapy, chemotherapy, photodynamic therapy, surgery or other immunotherapy The antibody and one or more additional therapeutic agents (the combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months and once every six months, or may be administered continuously via a minipump. The combination therapy may be administered via an oral, mucosal, buccal, intranasal, inhalable, intravenous, subcutaneous, intramuscular, parenteral, intratumor or topical route. The combination therapy may be administered at a site distant from the site of the tumor. The combination therapy generally will be administered for as long as the tumor is present provided that the antibody causes the tumor or cancer to stop growing or to decrease in weight or volume.

In a still further embodiment, the anti-IGF-IR antibody is labeled with a radiolabel, an immunotoxin or a toxin, or is a fusion protein comprising a toxic peptide. The anti-IGF-IR antibody or anti-IGF-IR antibody fusion protein directs the radiolabel, immunotoxin, toxin or toxic peptide to the IGF-IR-expressing tumor or cancer cell. In a preferred embodiment, the radiolabel, immunotoxin, toxin or toxic peptide is internalized after the anti-IGF-IR antibody binds to the IGF-IR on the surface of the tumor or cancer cell.

In another aspect, the anti-IGF-IR antibody may be used therapeutically to induce apoptosis of specific cells in a patient in need thereof. In many cases, the cells targeted for apoptosis are cancerous or tumor cells. Thus, in a preferred embodiment, the invention provides a method of inducing apoptosis by administering a therapeutically effective amount of an anti-IGF-IR antibody to a patient in need thereof. In a preferred embodiment, the antibody is 2.12.1fx, or comprises a heavy chain, light chain or antigen-binding region thereof.

In another aspect, the anti-IGF-IR antibody may be used to treat noncancerous states in which high levels of IGF-I and/or IGF-IR have been associated with the noncancerous state or disease. In one embodiment, the method comprises the step of administering an anti-IGF-IR antibody to a patient who has a noncancerous pathological state caused or exacerbated by high levels of IGF-I and/or IGF-IR levels or activity. In a preferred embodiment, the noncancerous pathological state is acromegaly, gigantism, psoriasis, atherosclerosis, smooth muscle restenosis of blood vessels or inappropriate microvascular proliferation, such as that found as a complication of diabetes, especially of the eye. In a more preferred embodiment, the anti-IGF-IR antibody slows the progress of the noncancerous pathological state. In a more preferred embodiment, the anti-IGF-IR antibody stops or reverses, at least in part, the noncancerous pathological state.

In another aspect, the invention provides a method of administering an activating anti-IGF-IR antibody to a patient in need thereof. In one embodiment, the activating antibody or pharmaceutical composition is administered to a patient in need thereof in an amount effective to increase IGF-IR activity. In a more preferred embodiment, the activating antibody is able to restore normal IGF-IR activity. In another preferred embodiment, the activating antibody may be administered to a patient who has small stature, neuropathy, a decrease in muscle mass or osteoporosis. In another preferred embodiment, the activating antibody may be administered with one or more other factors that increase cell proliferation, prevent apoptosis or increase IGF-IR activity. Such factors include growth factors such as IGF-I, and/or analogues of IGF-I that activate IGF-IR. In a preferred embodiment, the antibody is 2.12.1fx, or comprises a heavy chain, light chain or antigen-binding portion thereof.

The nucleic acid molecules of the instant invention may be administered to a patient in need thereof via gene therapy. The therapy may be either in vivo or ex vivo. In a preferred embodiment, nucleic acid molecules encoding both a heavy chain and a light chain are administered to a patient. In a more preferred embodiment, the nucleic acid molecules are administered such that they are stably integrated into the chromosome of B cells because these cells are specialized for producing antibodies. In a preferred embodiment, precursor B cells are transfected or infected ex vivo and re-transplanted into a patient in need thereof. In another embodiment, precursor B cells or other cells are infected in vivo using a virus known to infect the cell type of interest. Typical vectors used for gene therapy include liposomes, plasmids, or viral vectors, such as retroviruses, adenoviruses and adeno-associated viruses. After infection either in vivo or ex vivo, levels of antibody expression may be monitored by taking a sample from the treated patient and using any immunoassay known in the art and discussed herein.

In a preferred embodiment, the gene therapy method comprises the steps of administering an effective amount of an isolated nucleic acid molecule encoding the heavy chain or the antigen-binding portion thereof of the human antibody or portion thereof and expressing the nucleic acid molecule. In another embodiment, the gene therapy method comprises the steps of administering an effective amount of an isolated nucleic acid molecule encoding the light chain or the antigen-binding portion thereof of the human antibody or portion thereof and expressing the nucleic acid molecule. In a more preferred method, the gene therapy method comprises the steps of administering an effective amount of an isolated nucleic acid molecule encoding the heavy chain or the antigen-binding portion thereof of the human antibody or portion thereof and an effective amount of an isolated nucleic acid molecule encoding the light chain or the antigen-binding portion thereof of the human antibody or portion thereof and expressing the nucleic acid molecules. The gene therapy method may also comprise the step of administering another anti-cancer agent, such as taxol, tamoxifen, 5-FU, adriamycin or CP-358,774.

Sequence ID Nos. of the Application:

SEQ ID NO 1: DNA sequence encoding the heavy chain of antibody 2.12.1fx including the sequence encoding the signal sequence used to express the mature antibody.

SEQ ID NO 2: DNA sequence encoding the light chain of antibody 2.12.1fx including the sequence encoding the signal sequence used to express the mature antibody.

SEQ ID NO 3: Amino acid sequence of the heavy chain of antibody 2.12.1fx.

SEQ ID NO 4: Amino acid sequence of germlne DP-35.

SEQ ID NO 5: Amino acid sequence of the light chain of antibody 2.12.1fx.

SEQ ID NO 6: Amino acid sequence of germlne A30/Jkl.

In order that this invention may be better understood, the following examples are set forth. These examples are for purposes of illustration only and are not to be construed as limiting the scope of the invention in any manner.

EXAMPLE I

Generation of Hybridoma Producing Anti-IGF-IR Antibody

The antibody of the invention was prepared, selected, and assayed as follows:

Eight to ten week old XENOMICE™ were immunized intraperitoneally or in their hind footpads with either the extracellular domain of human IGF-IR (10 μg/dose/mouse), or with 3T3-IGF-IR or 300.19-IGF-IR cells, which are two transfected cell lines that express human IGF-IR on their plasma membranes ($10 \times 10^6$ cells/dose/mouse). This dose was repeated five to seven times over a three to eight week period. Four days before fusion, the mice received a final injection of the extracellular domain of human IGF-IR in PBS. Spleen and lymph node lymphocytes from immunized mice were fused with the non-secretory myeloma P3-X63-Ag8.653 cell line and were subjected to HAT selection as previously described (Galfre and Milstein, *Methods Enzymol.* 73:3-46, 1981). A hybridoma, 2.12.1, producing monoclonal antibodies specific for IGF-IR was selected for further study and deposited in the American Type Culture Collection (ATCC), 10801 University Boulevard, Manassas, Va. 20110-2209, on Dec. 12, 2000 with the following deposit number:

| Hybridoma | Deposit No. |
| --- | --- |
| 2.12.1 | PTA-2792 |

This hybridoma, and others producing antibodies specific for IGF-1R are described in WO 02/05359, published Jul. 11, 2002. The text of this publication, including all sequences described, is hereby incorporated by reference.

The antibody 2.12.1 produced by hybridoma 2.12.1 was generated from mice immunized with IGF-1R extracellular domain (ECD). Subsequently, recombinant mouse myeloma (NSO) cell lines expressing 2.12.1 were constructed following well-established molecular biology protocols. At this time, two framework mutations in the heavy chain, and three framework mutations in the light chain were corrected back to germ line to produce the antibody 2.12.1fx.

All changes to make 2.12.1fx mutations were done using QuikChange Site-Directed Mutagenesis Kit (Stratagene™) by preparing a plasmid with target site for mutation by denaturing the plasmid and annealing the oligonucleotide primers containing the desired mutation. The nonstrand-displacing action of Pfu Turbo DNA polymerase was used to extend and incorporate the mutagenic primers resulting in nicked circular strands. Digestion of the methylated, non-mutated parental DNA template with Dpnl was followed by transforming the circular, nicked dsDNA into XL1Blue supercompetent cells. After transformation, the XL1-Blue supercompetent cells repaired the nicks in the mutated plasmid. The plasmids containing mutations were selected and the sequence verified.

FIG. 1 shows the DNA sequence encoding the heavy chain of antibody 2.12.1fx, including the sequence encoding the signal sequence used to express the mature antibody (SEQ ID NO: 1). FIG. 2 shows the DNA sequence encoding the light chain of antibody 2.12.1fx, including the sequence encoding the signal sequence used to express the mature antibody (SEQ ID NO: 2). FIG. 3 shows an alignment of the amino acid sequence of the heavy chain of antibody 2.12.1fx (SEQ ID NO: 3) with that of germline sequence DP-35 (3-11)/D3-3/JH6 (SEQ ID NO: 4). The sequence of antibody 2.12.1fx is shown above that for the germline sequence. The signal sequences are in italics and the CDRs are underlined. The constant domain region begins with the amino acid residues ASTK and corresponds to amino acid residue 148 in the germline and extends to the end of the sequence. The framework (FR) mutations are amino acid residues 21 and 116. FIG. 4 shows an alignment of the amino acid sequence of the light chain of antibody 2.12.1fx (SEQ ID NO: 5) with that of germline sequence A30/Jk1 (SEQ ID NO: 6). The sequence of antibody 2.12.1fx is shown above that for the germline sequence. The signal sequences are in italics and the CDRs are underlined. The constant domains region begins with the amino acid residues TVAA and corresponds to amino acid residue 131 in the germline and extends to the end of the sequence. The framework (FR) mutations are amino acid residues 43, 125, and 129.

EXAMPLE II

Antibody-mediated Blocking of IGF-I/IGF-IR Binding

ELISA experiments were performed to quantitate the ability of the antibody of the invention to inhibit IGF-I binding to IGF-IR in a cell-based assay. IGF-IR-transfected NIH-3T3 cells ($5\times10^4$/ml) were plated in 100 µl of DMEM high glucose media supplemented with L-glutamine (0.29 mg/ml), 10% heat-inactivated FBS, and 500 µg/ml each of geneticin, penicillin and streptomycin in 96-well U-bottom plates. The plates were incubated at 37° C., 5% $CO_2$ overnight to allow cells to attach. The media was decanted from the plates and replaced with 100 µl fresh media per well. For testing, the antibody was diluted in assay media (DMEM high glucose media supplemented with L-glutamine, 10% heat-inactivated FBS, 200 µg/ml BSA and 500 µg/ml each of geneticin, penicillin and streptomycin) to the desired final concentration. All samples were performed in triplicate. The plates were incubated at 37° C. for ten minutes. The [$^{125}$I]-IGF-I was diluted to a concentration of 1 µCi/ml in assay media and added 50 µl per well of the plate. As a control for background radioactivity, cold IGF-I was added to a final concentration of 100 ng/ml. The plates were incubated for 10 minutes at 37° C. and the media decanted by blotting gently onto paper towels and washing twice with assay media. The cells were lysed by adding 50 µl 0.1 N NaOH, 0.1% SDS and the plates shaken for five minutes at room temperature. The samples were transferred to a scintillation plate, 150 µl OptiPhase Supermix was added and the signal was read using a Wallace Micro-Beta counter.

Table I and FIG. 5 show the results of this experiment performed with the antibody of this invention. This experiment demonstrated that the antibody of the invention specifically inhibits binding of [$^{125}$I]-IGF-I to cells overexpressing IGF-IR.

TABLE I

| Monoclonal Antibody | $IC_{50}$ |
|---|---|
| 2.12.1fx | 0.4 µg/ml |

EXAMPLE III

Antibody-mediated Inhibition of IGF-I-induced Phosphorylation of IGF-IR

ELISA experiments were performed in order to determine whether the antibody of this invention was able to block IGF-I-mediated activation of IGF-IR. IGF-I-mediated activation of IGF-IR was detected by decreased receptor-associated tyrosine phosphorylation.

ELISA Plate Preparation

ELISA capture plates were prepared by adding 100 µl blocking buffer (3% bovine serum albumin [BSA] in Tris-buffered saline [TBS]) to each well of a ReactiBind Protein G-coated 96-well plates (Pierce). The plates were incubated by shaking for 30 minutes at room temperature. The rabbit pan-specific SC-713 anti-IGF-IR antibody (Santa Cruz) was diluted in blocking buffer to a concentration of 5 /µg/ml. 100 µl diluted antibody was added to each well. The plates were incubated with shaking for 60-90 minutes at room temperature. The plates were washed five times with wash buffer (TBS+0.1% Tween 20) and the remaining buffer was blotted out onto paper towels. These plates were not allowed to dry out prior to the addition of lysate.

Preparation of Lysate from IGF-IR-expressing Cells

The IGF-IR-transfected NIH-3T3 cells ($5\times10^4$/ml) were placed in 100 µl of growth media (DMEM high glucose media supplemented with L-glutamine (0.29 mg/ml), 10% heat-inactivated FBS, and 500 µg/ml each of geneticin, penicillin and streptomycin) in 96-well U-bottom plates. The plates were incubated at 37° C., 5% $CO_2$ overnight to allow the cells to attach. The media was decanted from the plates and replaced with 100 µl fresh growth media per well. For testing, the potential anti-IGF-IR antibodies were diluted to five times the desired final concentration in growth media and 25 µl were added per well. All samples were performed in triplicate. The plates were incubated at 37° C. for one hour. The cells were stimulated with 25 µl/well of 600 ng/ml IGF-1 (prepared in growth media) and incubated at room temperature for 10 minutes. The media was decanted by inverting the plates and blotting gently onto paper towels. The adherent cells were lysed by adding 50 µl of lysis buffer (50 mM HEPES, pH 7.4, 10 mM EDTA, 150 mM NaCl, 1.5 mM MgCl$_2$, 1.6 mM NaVO$_4$, 1% Triton X-100, 1% glycerol) and supplemented immediately before use with one EDTA-free protease inhibitor tablet [Roche Molecular Sciences] per 50 ml). The cell were shaken for 5 minutes at room temperature. 200 µl dilution buffer (50 mM HEPES, pH 7.4, 1.6 mM NaVO$_4$) was added to each well and mixed by pipetting. 100 µl of lysate was transferred from each well to each well of the ELISA capture plate prepared as described above and incubated with gentle shaking for two hours at room temperature.

ELISA with Anti-Phosphotyrosine (pTYR) Antibodies

The cell lysate was removed by inverting the plates, washing the plates five times with wash buffer and blotting excess liquid on paper towels. 100 µl per well of pTYR-specific antibody (HRP-PY54) was added and diluted in blocking buffer to a concentration of 0.2 pg/ml. The cells were incubated by shaking the plates for 30 minutes at room temperature. The plates were then washed five times with wash buffer and blotted on paper towels.

Binding of the HRP-PY54 antibody was detected by adding 100 µl per well of TMB peroxidase substrate solution (Kirkegaard & Perry) and incubating with shaking as the color developed (approximately 2-10 minutes). The color development reaction was stopped by adding 100 µl per well of TMB stop solution (Kirkegaard & Perry). The plates were shaken for 10 seconds at room temperature to mix the solution and quantitated by measurement at OD$_{450nm}$.

Table II and FIG. 6A show the results of this experiment with the antibody of the invention. The results of this experiment demonstrate the ability of the antibody of this invention to block IGF-I-mediated activation of IGF-IR as shown by decreased receptor-associated tyrosine phosphorylation. Furthermore, these results can be used to quantify the relative potency of the antibody of this invention.

TABLE II

| Monoclonal Antibody | IC$_{50}$ (µg/ml) |
|---|---|
| 2.12.1fx | 0.42 |

EXAMPLE IV

Species Crossreactivity of the Antibody of the Invention

In order to determine the species crossreactivity of the antibody of the invention, several experiments were performed including immunoprecipitation, antibody-mediated blocking of IGF-I-induced receptor phosphorylation and FACS analysis.

To perform immunoprecipitation experiments, cells were plated in DMEM high glucose media supplemented with L-glutamine (0.29 mg/ml), 10% heat-inactivated FBS, and 500 µg/ml each of geneticin, penicillin and streptomycin to 50% confluence in T25 flasks. 100 µl of an antibody of the invention in Hank's buffered saline solution (HBSS; Gibco BRL) at a concentration of 1 µg/ml was added. The plates were incubated for 30 minutes at 37° C. in an incubator and then stimulated cells with IGF-I at 100 ng/ml for 10 minutes at room temperature. The cells were lysed in RIPA buffer (Harlow and Lane, supra) and immunoprecipitated the IGF-IR with 2 pg of pan-specific SC-713 anti-IGF-IR antibody (Santa Cruz) plus protein A agarose beads for 1 hour at 4° C. The beads were pelleted and washed three times with PBS/T (PBS+0.1% Tween-20) and then boiled in 40 µl Laemmli buffer containing 5% βME.

The samples prepared as described above were then analyzed by Western blot. 12 µl of each sample were loaded per lane on 4-10% gradient Novex™ gels run with 1×MES buffer (Novex™). Gels were run at 150V for 1 hour or at 200V for approximately 30 minutes. The gel was transferred to a membrane in Novex™ transfer buffer with 10% methanol either overnight at 100 mA or for 1-1.5 hours at 250 mA. The membrane was allowed to dry completely and blocked at room temperature with TBS (Tris-buffered saline pH 8.0) containing Superblock (Pierce Chemical Co.). The IGF-IR blotting antibody SC713 (Santa Cruz) or a phosphotyrosine antibody was added to detect immunoprecipitated IGF-IR or phospho-IGF-1R respectively.

This experiment was performed with the antibody of the invention on cells from a variety of animals. The antibody was able to bind human, but not canine and mouse IGF-IR. These experiments indicate that the antibodies are highly specific.

Determination of Cross-species Affinity of Antibodies of the Invention

FACS analysis was performed to determine the affinity of the antibody of the invention for IGF-IR from other animals, particularly the old world monkeys described above. Aliquots of human and monkey cells (cynomolgus) (5×10$^5$) were incubated for 1 hour on ice with increasing concentrations of biotinylated anti-IGF-IR antibodies of the invention. The samples were incubated for 30 minutes on ice with streptavidin-conjugated RPE (phycoerythrin). Binding was measured by flow cytometry and analyzed with the histograms of fluorescence intensity (FI2-H) versus cell number (Counts) using CellQuest software. Binding (K$_d$) was calculated for each antibody from graphs of mean fluorescence intensity versus antibody concentration. In most experiments, binding was measured in cultured human MCF-7 cells and cynomolgus tissue culture cells. Depletion of the antibody was controlled by measuring binding over a range of cell concentrations.

The aforementioned FACS analysis was performed to test the ability of the antibody of the invention to bind human and cynomolgus cells. A half maximal binding (K$_d$) of 0.1 µg/ml for all cell lines tested was observed.

EXAMPLE V

IGF-I Receptor Downregulation

To investigate whether the antibody of the invention could induce the down regulation of IGF-1R on cells, MCF7 cells were plated in DMEM/F12 media supplemented with L-glutamine (0.29 mg/ml), 10% heat-inactivated FBS, penicillin and streptomycin to 50% confluence in T75 flasks. The antibody of the invention was added to the cells at a final concentration of 1 µg/ml. The plates were incubated for designated hours at 37° C. in an incubator and then lysed in 50 mM HEPES, pH 7.4, 10 mM EDTA, 150 mM NaCl, 1.5 mM MgCl$_2$, 1.6 mM NaVO$_4$, 1% Triton X-100, 1% glycerol. The level of total IGF-1R within the cell extracts was determined by western blot analysis using the pan-specific SC-713 anti-IGF-IR antibody (Santa Cruz). See FIG. 6B. Treatment of the MCF7 cells with the antibody of the invention resulted in 60-70 percent downregulation of IGF-1R with 1-2 hours.

EXAMPLE VI

Effects of the Antibody of the Invention on IGF-IR in Vivo

An experiment was performed to determine whether the effects of the antibody of the invention on IGF-IR as described in the previous examples would occur in vivo. Tumors were induced in athymic mice according to published methods (V. A. Pollack et al., "Inhibition of epidermal growth factor receptor-associated tyrosine phosphorylation in human carcinomas with CP-358,774: Dynamics of receptor inhibition in situ and antitumor effects in athymic mice," *J. Pharmacol. Exp. Ther.* 291:739-748 (1999). Briefly, IGF-IR-transfected NIH-3T3 cells ($5 \times 10^6$) were injected subcutaneously into 3-4 week-old athymic (nu/nu) mice with 0.2 ml of Matrigel preparation. The mice were then injected with an antibody of the invention intraperitoneally after established (i.e. approximately 400 mm3) tumors formed.

After 24 hours, the tumors were extracted, homogenized, and the level of IGF-IR determined. To determine IGF-IR levels, the SC-713 antibody was diluted in Blocking buffer to a final concentration of µg/ml and 100 µl was added to each well of a Reacti-Bind Goat anti-rabbit (GAR) coated plate (Pierce). The plates were incubated at room temperature for 1 hour with shaking and then washing five times with wash buffer. The tumor samples were weighed. 12.5 µl of tumor extract were diluted with lysis buffer to a final volume of 100 µl. A sample of 100 µl was added to each well of a 96-well plate. The plates were incubated at room temperature with shaking for 1-2 hours and then washed five times with Wash buffer. 100 µl HRP-PY54 or biotinylated anti-IGF-IR antibody in Blocking buffer was added to each well and incubated at room temperature with shaking for 30 minutes. The plates were washed five times with wash buffer and developed. The plates were developed by probing with HRP-PY54 by adding 100 µl of the TMB microwell substrate per well and color development stopped with the addition 100 µl 0.9 M $H_2SO_4$. The signal was quantitated by shaking for 10 seconds and measuring OD450 nm. The signal was normalized to total protein. Plates probed with anti-IGF1R antibody were developed by adding 100 µl of streptavidin-HRP diluted in Blocking buffer to each well, incubating at room temperature with shaking for 30 minutes and then continuing as described for HRP-PY54.

Figure 7:
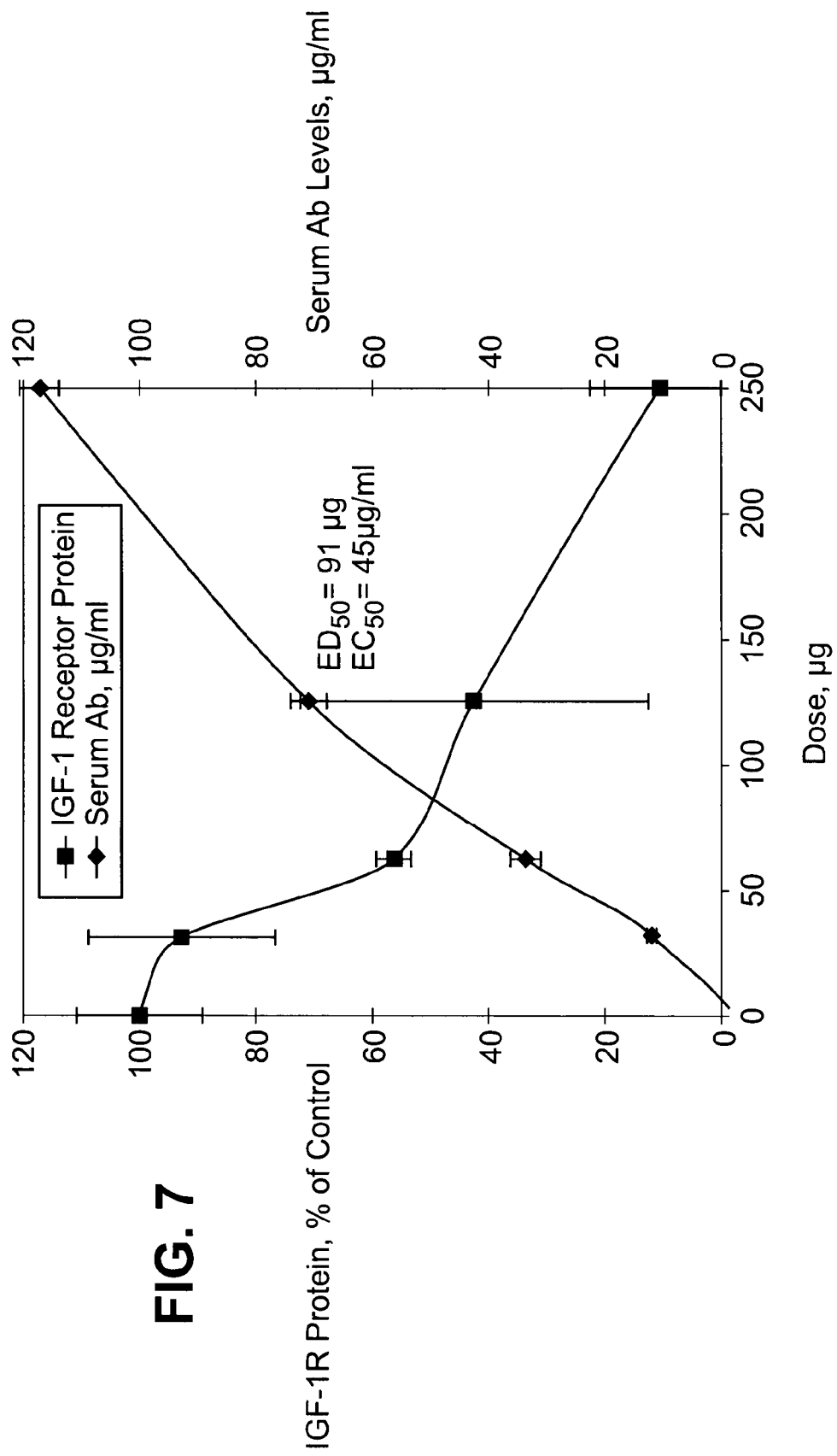
FIG. 7 shows that anti-IGF-IR antibody 2.12.1fx reduces IGF-IR level in 3T3-IGF-IR tumors.

It was observed that intraperitoneal injection of the antibody of the invention, resulted in inhibition of IGF-IR activity as measured by a decrease of IGF-IR protein (FIG. 7). Furthermore, this inhibition was responsive to the dose of antibody injected (FIG. 7). These data demonstrate that the antibody of the invention is able to target the IGF-IR in vivo in a manner to that observed in vitro.

EXAMPLE VII

Growth Inhibition (TGI) of 3T3/IGF-IR Cell Tumors

The antibody of the invention was tested to determine if it would function to inhibit tumor growth. Tumors were induced as described above (Example VI) and when established, palpable tumors formed (i.e. 250 mm³, within 6-9 days). The mice were treated with a single, 0.20 ml dose of antibody by intraperitoneal injection. Tumor size was measured by Vernier calipers across two diameters every third day and volume calculated by using the formula (length× [width]²)/2 using methods established by Geran, et al., "Protocols for screening chemical agents and natural products against animal tumors and other biological systems," *Cancer Chemother. Rep.* 3:1-104.

Figure 8A:
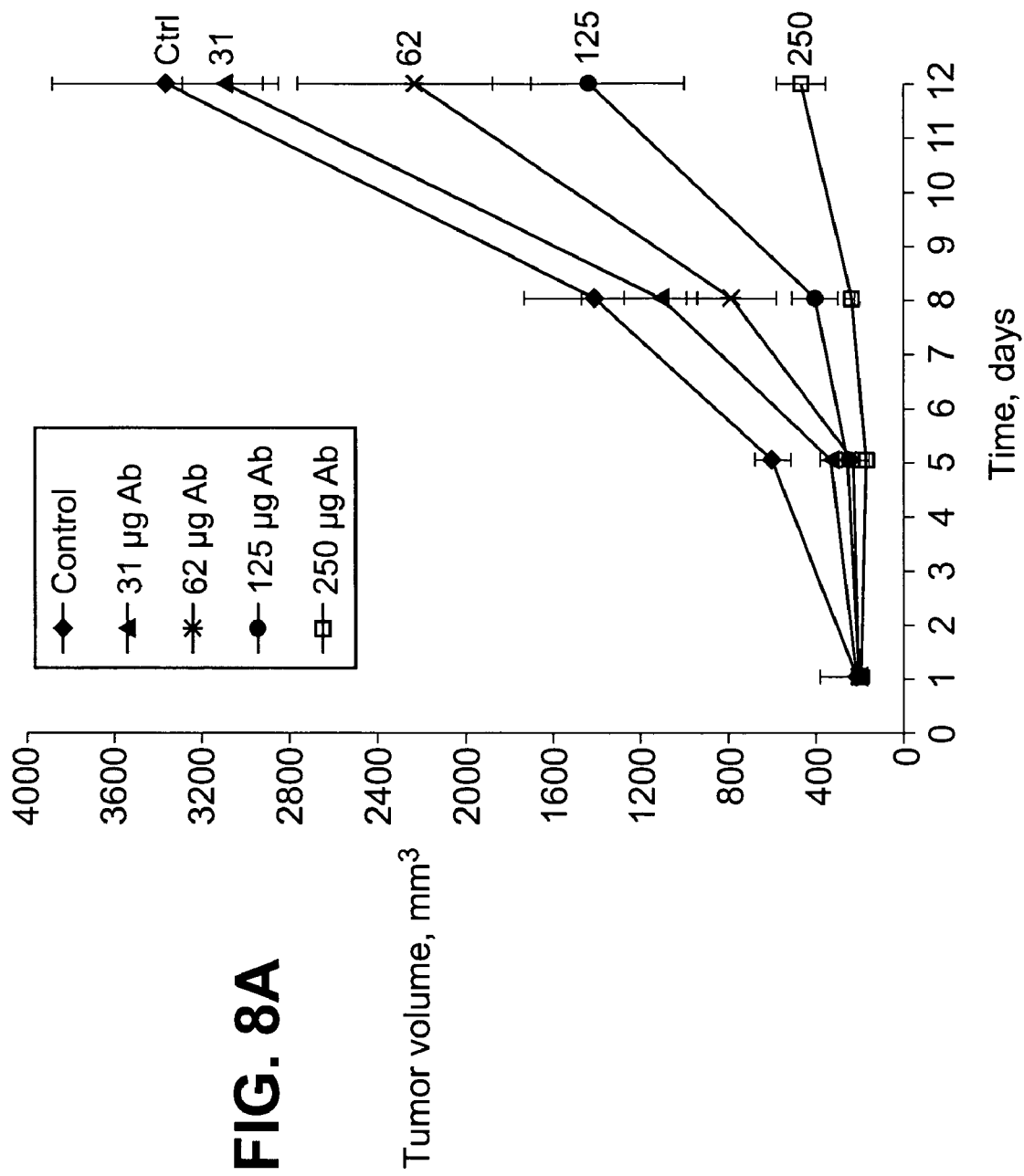

Following the analysis with the antibody of the invention it was observed that a single treatment with the antibody alone inhibited the growth of IGF-IR-transfected NIH-3T3 cell-induced tumors (FIG. 8A). Furthermore, in combination studies with a single dose of 7.5 mg/kg intravenously-supplied adriamycin, it was observed that administration of a single dose of the antibody enhanced the effectiveness of adriamycin, a known inhibitor of tumor growth. The combination of adriamycin with the antibody of the invention demonstrated a growth delay of 7 days versus treatment with the antibody or adriamycin alone (FIG. 8B).

EXAMPLE VIII

Relationship of Antibody Levels to IGF-IR Downregulation

Figure 9:
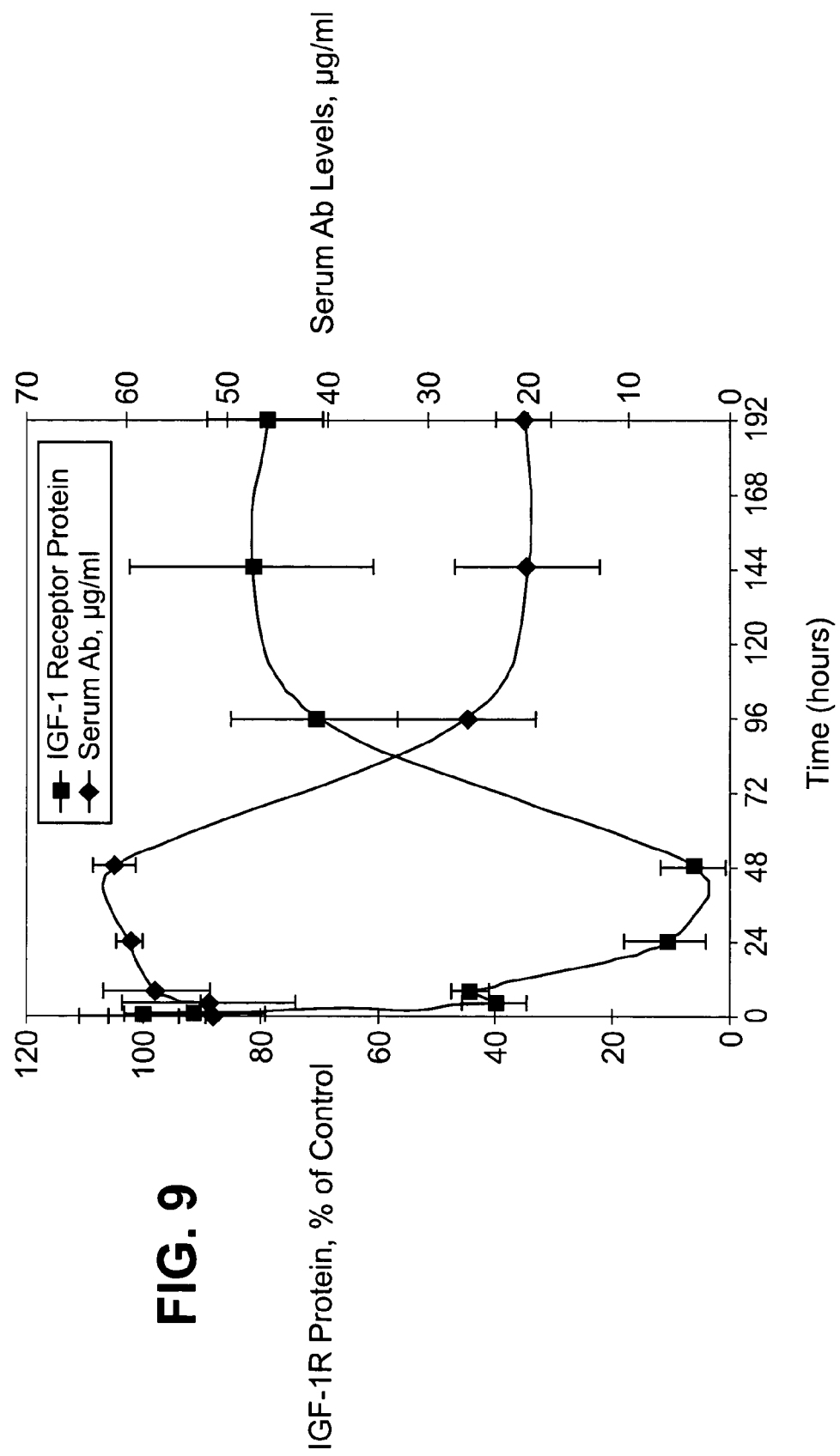
FIG. 9 shows the relationship between anti-IGF-IR antibody 2.12.1fx serum levels and IGF-IR downregulation over time in 3T3-IGF-IR tumors.

Tumors were induced in nude mice as described in Example VI. The mice were then treated with 125 µg of the antibody by intraperitoneal injection, as described in Example VI. Tumors were extracted and IGF-IR levels were measured by ELISA. FIG. 9 shows the serum antibody levels and IGF-IR receptor levels over time. The experiment demonstrates that the IGF-IR is down-regulated by the antibody and that the degree of IGF-IR inhibition is dose proportional to the serum concentration of the antibody.

EXAMPLE IX

Growth Inhibition of Colorectal Cell Tumors

Figure 10A:
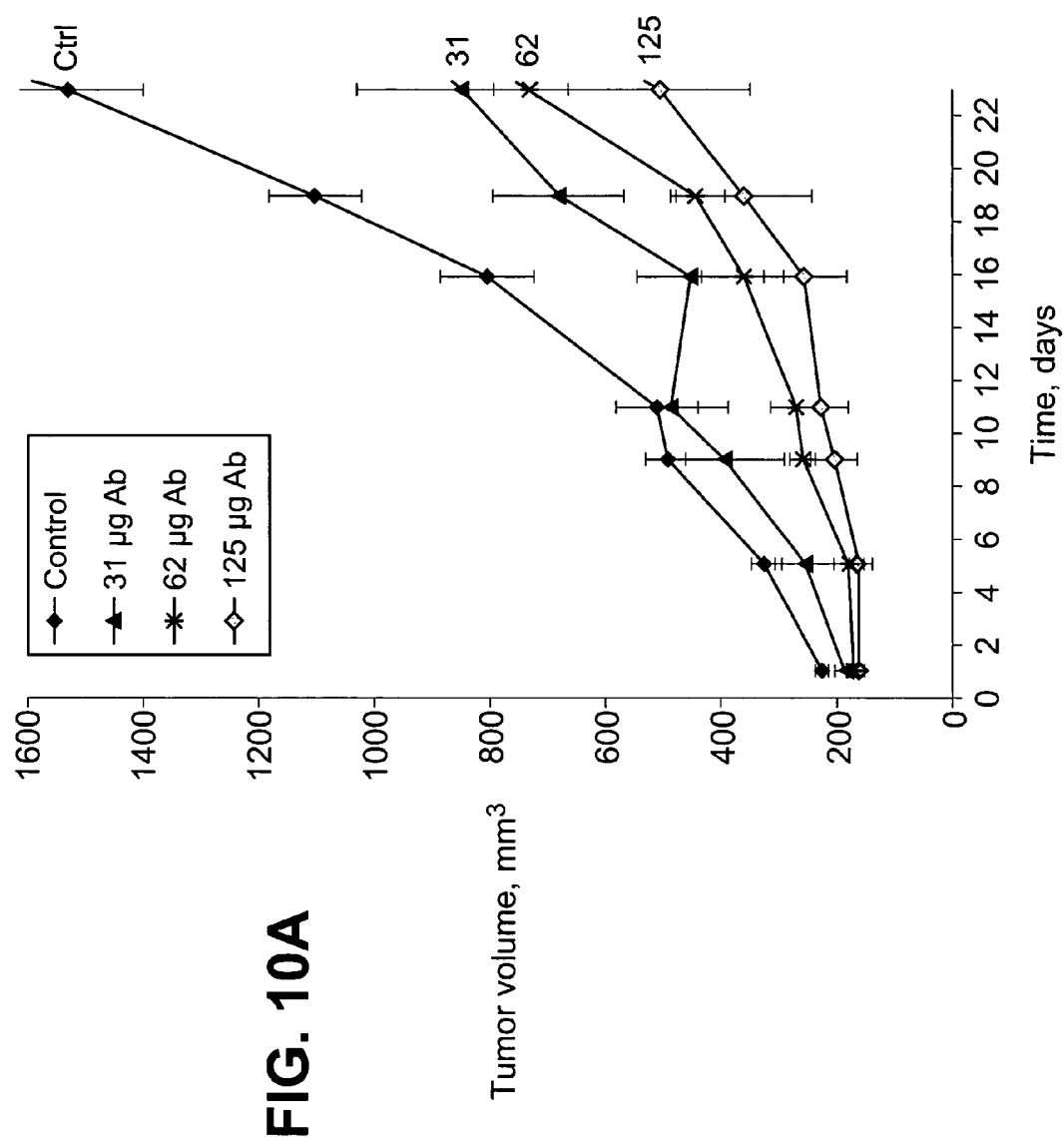
FIGS. 10A and 10B show that anti-IGF-IR antibody 2.12.1fx inhibits Colo 205 tumor growth in vivo alone (FIG. 10A) or in combination with 5-fluorodeoxyuridine (5-FU) (FIG. 10B).
Figure 10B:
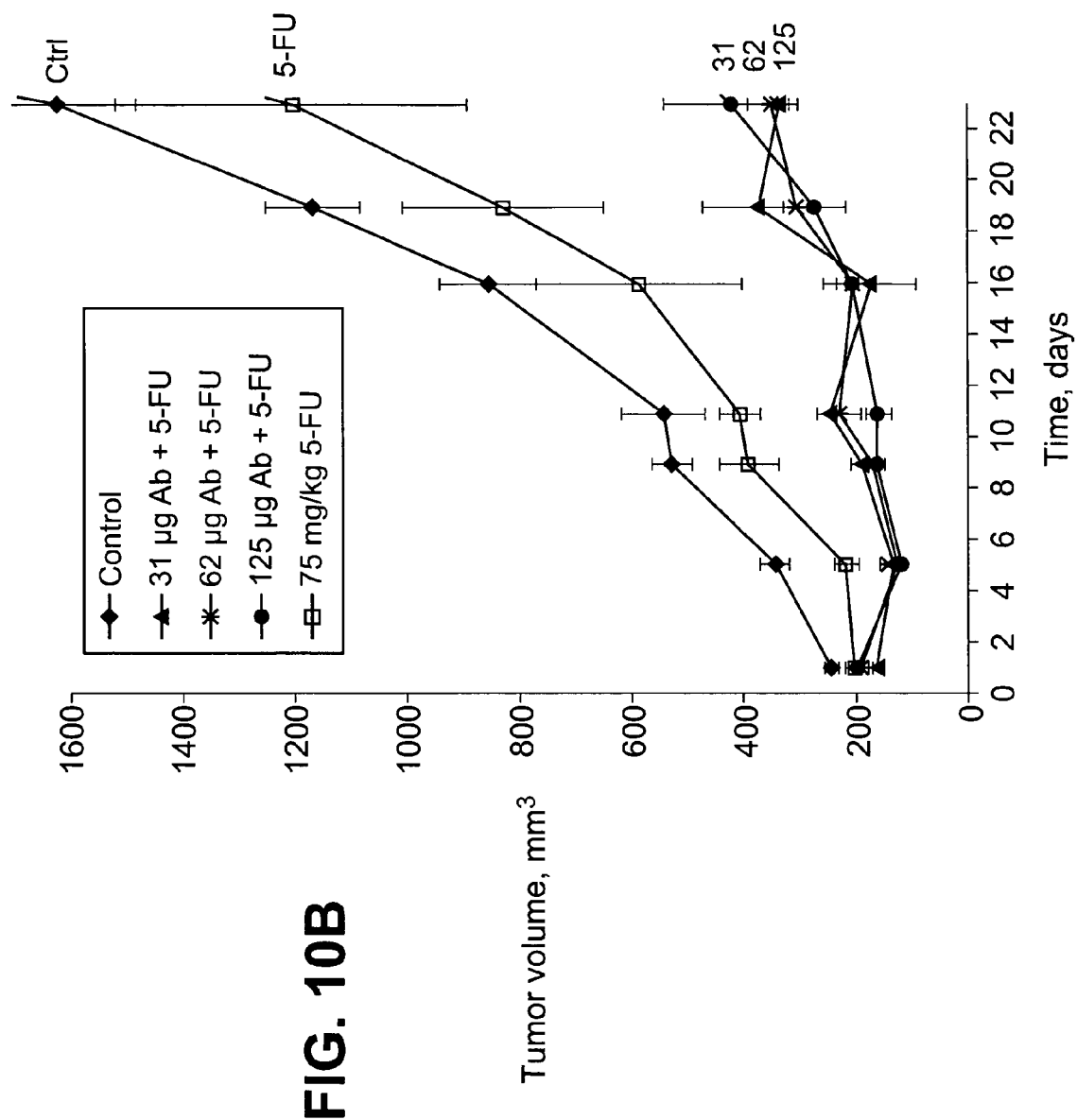

Tumors were induced in nude mice as described in Example VI except that Colo 205 cells (ATCC CCL 222) were used. Colo 205 cells are human colorectal adenocarcinoma cells. Mice with established subcutaneous tumors of approximately 250 mm³ were treated with various amounts of the antibody (i.p.) or with 100 mg/kg 5-fluorodeoxyuridine (5-FU, i.v.), either as single agents or in combination, as described in Example VII. FIG. 10A and FIG. 10B show the tumor size in relation to the various treatments over time. The experiment demonstrates that treatment with an anti-IGF-IR antibody given once inhibits human colorectal cancer cell growth when provided as a single agent and enhances the effectiveness of 5-FU, a known tumor inhibitor.

EXAMPLE X

Pharmacokinetics of Anti-IGF-IR Antibodies in Vivo

Figure 11:
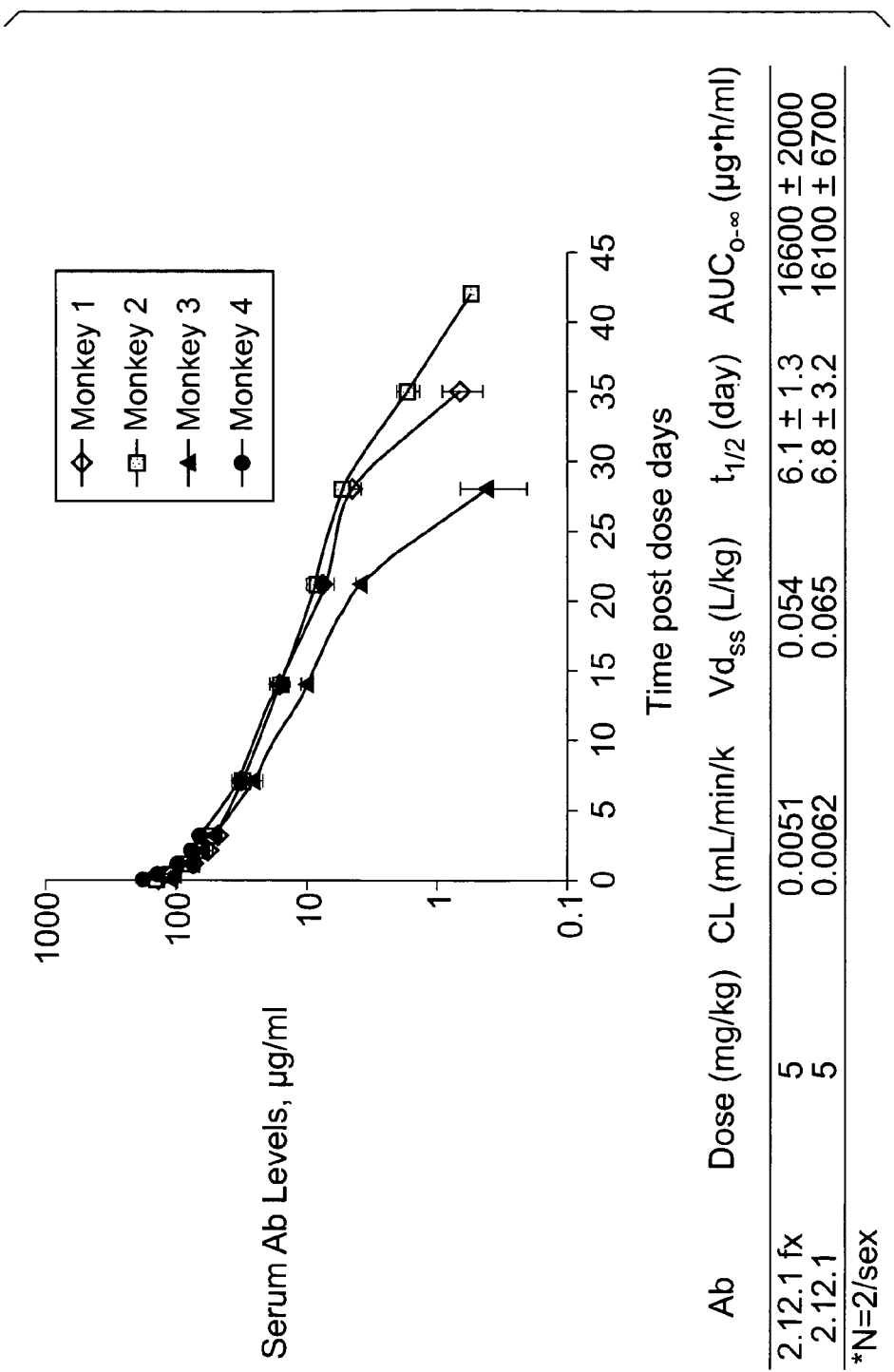
FIG. 11 shows a pharmacokinetic evaluation of a single intravenous injection of anti-IGF-IR antibody 2.12.1fx in Cynomolgus monkeys.

To evaluate the pharmacokinetics of the anti-IGF-IR antibodies, cynomolgus monkeys were injected intravenously with 5 mg/kg of the antibody in an acetate buffer. Serum was collected from the monkeys at various time points and anti-IGF-IR antibody concentrations in the monkeys were determined for a period of up to ten weeks. To quantitate functional serum antibody levels, the extracellular domain of the human IGF-IR (IGF-I-sR, R&D Systems, Catalog # 391GR) was bound to 96-well plates. Monkey serum (diluted between 1:100 and 1:15,000) was added to the assay plates so that each sample would be within the linear range of the standard curve and incubated under conditions in which any anti-IGF-IR antibody would bind to IGF-I-sR. After washing the plates, a labeled anti-human IgG antibody was added to the plates and incubated under conditions in which the anti-human IgG antibody would bind to the anti-IGF-IR antibody. The plates were then washed and developed, and a control standard curve and linear regression fit used to quantitate the amount of anti-IGF-IR antibodies. FIG. 11 shows the concentration of the antibody in serum over time. The experiment demonstrates that the half-life ($t_{1/2}$) of the anti-IGF-IR antibody is 6.1 days and has a volume distribution ($Vd_{ss}$) of 0.054 (L/kg).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A human antibody or antigen-binding portion thereof, comprising: (i) a light chain variable region that comprises three framework mutations reverted back to an amino acid sequence encoded by a germ line A30 gene and (ii) a heavy chain variable region that comprises two framework mutations reverted back to amino acid sequence encoded by a germ line DP-35 gene, wherein the antibody or antigen-binding portion thereof specifically binds to human insulin-like growth factor I receptor (IGF-1R), and wherein the light chain variable region comprises amino acid numbers 23 to 130 of SEQ ID NO: 5 and the heavy chain variable region comprises amino acid numbers 20 to 144 of SEQ ID NO: 3.

2. The human antibody or antigen-binding portion thereof according to claim 1, wherein the light chain comprises amino acid numbers 23 to 236 of SEQ ID NO: 5 and the heavy chain comprises amino acid numbers 20 to 470 of SEQ ID NO: 3.

3. A human monoclonal antibody or antigen-binding portion thereof that specifically binds to human IGF-1R, comprising at least one somatically mutated amino acid residue in a framework region of a variable region of said antibody that has been replaced by a corresponding germline amino acid residue, wherein the heavy chain comprises amino acid numbers 20 to 470 of SEQ ID NO: 3 and the light chain comprises amino acid numbers 23 to 236 of SEQ ID NO: 5.

4. A pharmaceutical composition for the treatment of cancer comprising the antibody or antigen-binding portion thereof according to any one of claims 1, 2, or 3 and a pharmaceutically acceptable carrier.

5. The pharmaceutical composition according to claim 4, further comprising an antineoplastic, chemotherapeutic or anti-tumor agent.

* * * * *